(12) United States Patent
Farha et al.

(10) Patent No.: US 9,610,560 B2
(45) Date of Patent: Apr. 4, 2017

(54) METAL-ORGANIC FRAMEWORK COMPOUNDS WITH LIGAND-FUNCTIONALIZED METAL NODES

(71) Applicant: Northwestern University, Evanston, IL (US)

(72) Inventors: Omar K. Farha, Glenview, IL (US); Joseph T. Hupp, Northfield, IL (US); Pravas Deria, Evanston, IL (US)

(73) Assignee: Northwestern University, Evanston, IL (US)

( * ) Notice: Subject to any disclaimer, the term of this patent is extended or adjusted under 35 U.S.C. 154(b) by 46 days.

(21) Appl. No.: 14/611,641

(22) Filed: Feb. 2, 2015

(65) Prior Publication Data
US 2015/0217268 A1    Aug. 6, 2015

Related U.S. Application Data

(60) Provisional application No. 61/934,981, filed on Feb. 3, 2014.

(51) Int. Cl.
| | | |
|---|---|---|
| B01J 20/22 | (2006.01) |
| C07F 7/00 | (2006.01) |
| B01J 20/30 | (2006.01) |
| B01D 53/02 | (2006.01) |

(52) U.S. Cl.
CPC ............ B01J 20/226 (2013.01); B01D 53/02 (2013.01); B01J 20/3085 (2013.01); C07F 7/003 (2013.01); *B01D 2253/204* (2013.01); *B01D 2257/504* (2013.01); *B01D 2258/0283* (2013.01); *Y02C 10/08* (2013.01); *Y02P 20/152* (2015.11)

(58) Field of Classification Search
CPC .. B01D 53/02; B01D 53/04; B01D 2253/204; B01D 2257/504; B01D 2258/0283; B01J 20/226; B01J 20/3085; C07F 7/003; Y02C 10/08
USPC ............................ 95/139; 502/401; 423/230
See application file for complete search history.

(56) References Cited

U.S. PATENT DOCUMENTS

| | | | |
|---|---|---|---|
| 8,715,395 B2 * | 5/2014 | Omary ................. | B01D 53/02 548/101 |
| 8,962,875 B2 | 2/2015 | Norman et al. | |
| 2006/0252641 A1 | 11/2006 | Yaghi et al. | |
| 2011/0046335 A1 * | 2/2011 | Fernandes ............. | C08G 79/00 528/9 |

(Continued)

FOREIGN PATENT DOCUMENTS

EP    2578593    4/2013

OTHER PUBLICATIONS

Burnett et al., Stepwise Synthesis of Metal-Organic Frameworks: Replacement of Structural Organic Linkers, J. Am. Chem. Soc., vol. 133, Jun. 15, 2011, pp. 9984-9987.

(Continued)

*Primary Examiner* — Frank Lawrence
(74) *Attorney, Agent, or Firm* — Bell & Manning, LLC

(57) ABSTRACT

Metal-organic framework compounds (MOFs) coordinated to carbon-containing ligands, such as carboxylate ligands and phosphonate ligands, are provided. Also provided are methods for making the ligand-coordinated MOFs and methods for using the ligand-coordinated MOFs in carbon dioxide sequestration.

34 Claims, 11 Drawing Sheets

(56) References Cited

U.S. PATENT DOCUMENTS

| | | | |
|---|---|---|---|
| 2011/0297558 A1* | 12/2011 | Hill | B01D 53/02 |
| | | | 206/0.7 |
| 2012/0201860 A1 | 8/2012 | Weimer et al. | |
| 2012/0297982 A1 | 11/2012 | Dinca et al. | |
| 2013/0139686 A1* | 6/2013 | Wilmer | B01J 20/223 |
| | | | 95/127 |
| 2013/0296162 A1* | 11/2013 | Wright | B01J 20/226 |
| | | | 502/167 |
| 2015/0031908 A1* | 1/2015 | Bury | B01J 20/3236 |
| | | | 558/374 |

OTHER PUBLICATIONS

Bury et al., Control over Catenation in Pillared Paddlewheel Metal-Organic Framework Materials via Solvent-Assisted Linker Exchange, Chem. Mater., vol. 25, Feb. 9, 2013, pp. 739-744.

Dalvi et al., Understanding the Effectiveness of Fluorocarbon Ligands in Dispersing Nanoparticles in Supercritical Carbon Dioxide, J. Phys. Chem. C, vol. 114, Aug. 31, 2010, pp. 15553-15561.

Deria et al., Perfluoroalkane Functionalization of NU-1000 via Solvent-Assisted Ligand Incorporation: Synthesis and CO2 Adsorption Studies, J. Am. Chem. Soc., vol. 135, Oct. 31, 2013, pp. 16801-16804.

DeSimone et al., Dispersion Polymerizations in Supercritical Carbon Dioxide, Science, vol. 265, Jul. 15, 1994, pp. 356-359.

Farha et al., An Example of Node-Based Postassembly Elaboration of a Hydrogen-Sorbing, Metal-Organic Framework Material, Inorg. Chem., vol. 47, Oct. 18, 2008, pp. 10223-10225.

Fernandez et al., Gas-Induced Expansion and Contraction of a Fluorinated Metal-Organic Framework, Crystal Growth & Design, vol. 10, No. 3, Jan. 29, 2010, pp. 1037-1039.

Fried et al., The molecular basis of CO2 interaction with polymers containing fluorinated groups: computational chemistry of model compounds and molecular simulation of poly[bis(2,2,2-trifluoroethoxy)phosphazene], Polymer, vol. 44, 2003, pp. 4363-4372.

Hwang et al., Amine Grafting on Coordinatively Unsaturated Metal Centers of MOFs: Consequences for Catalysis and Metal Encapsulation, Angew. Chem. Int. Ed., vol. 47, Apr. 24, 2008, pp. 4144-4148.

Seo et al., A homochiralmetal-organic porous material for enantioselective separation and catalysis, Nature, vol. 404, Apr. 27, 2000, pp. 982-986.

Kanoo et al., Unusual room temperature CO2 uptake in a fluoro-functionalized MOF: insight from Raman spectroscopy and theoretical studies, Chem. Commun., vol. 48, Jun. 29, 2012, pp. 8487-8489.

Karagiaridi et al., Opening ZIF-8: A Catalytically Active Zeolitic Imidazolate Framework of Sodalite Topology with Unsubstituted Linkers, J. Am. Chem. Soc., vol. 134, Oct. 22, 2012, pp. 18790-18796.

Karagiaridi et al., Synthesis and characterization of isostructural cadmium zeolitic imidazolate frameworks via solvent-assisted linker exchange, Chem. Sci., vol. 3, Aug. 7, 2012, pp. 3256-3260.

Kiang et al., Variable Pore Size, Variable Chemical Functionality, and an Example of Reactivity within Porous Phenylacetylene Silver Salts, J. Am. Chem. Soc., vol. 121, Aug. 25, 1999, pp. 8204-8215.

Kim et al., Postsynthetic ligand exchange as a route to functionalization of 'inert' metal-organic frameworks, Chem. Sci., vol. 3, Sep. 13, 2011, pp. 126-130.

Li et al., Stepwise Ligand Exchange for the Preparation of a Family of Mesoporous MOFs, J. Am. Chem. Soc., vol. 135, May 20, 2013, pp. 11688-11691.

Mondloch et al., Vapor-Phase Metalation by Atomic Layer Deposition in a Metal-Organic Framework, J. Am. Chem. Soc., vol. 135, Jul. 5, 2013, pp. 10294-10297.

Noro et al., Highly Selective CO2 Adsorption Accompanied with Low-Energy Regeneration in a Two-Dimensional Cu(II) Porous Coordination Polymer with Inorganic Fluorinated PF6-Anions, Inorg. Chem., vol. 52, Dec. 18, 2012, pp. 280-285.

Nugent et al., Porous materials with optimal adsorption thermodynamics and kinetics for CO2 separation, Nature, vol. 495, Feb. 27, 2013, pp. 80-84.

Takaishi et al., Solvent-assisted linker exchange (SALE) and post-assembly metallation in porphyrinic metal-organic framework materials, Chem. Sci., vol. 4, Dec. 7, 2012, pp. 1509-1513.

Wilmer et al., Structure-property relationships of porous materials for carbon dioxide separation and capture, Energy Environ. Sci., vol. 5, Sep. 21, 2012, pp. 9849-9856.

Xue et al., Tunable Rare-Earth fcu-MOFs: A Platform for Systematic Enhancement of CO2 Adsorption Energetics and Uptake, J. Am. Chem. Soc., vol. 135, Apr. 22, 2013, pp. 7660-7667.

Yang et al., Fluorous Metal-Organic Frameworks with Superior Adsorption and Hydrophobic Properties toward Oil Spill Cleanup and Hydrocarbon Storage, J. Am. Chem. Soc., vol. 133, Oct. 7, 2011, pp. 18094-18097.

Yaghi et al., Reticular synthesis and the design of new materials, Nature, vol. 423, Jun. 12, 2003, pp. 705-714.

G. Ferey, Hybrid porous solids: past, present, future, Chemical Society Reviews, vol. 37, Sep. 19, 2007, pp. 191-214.

Horike et al., Soft porous crystals, Nature Chemistry, vol. 1, Nov. 23, 2009, pp. 695-704.

Lee et al., Metal-organic framework materials as catalysts, Chemical Society Reviews, vol. 38, Mar. 17, 2009, pp. 1450-1459.

Dinca et al., Hydrogen Storage in Microporous Metal-Organic Frameworks with Exposed Metal Sites, Angewandte Chemie Int. Ed., vol. 47, Aug. 8, 2008, pp. 6766-6779.

Bae et al., High Propene/Propane Selectivity in Isostructural Metal-Organic Frameworks with High Densities of Open Metal Sites, Angewandte Chemie Int. Ed., vol. 51, Jan. 16, 2012, pp. 1857-1860.

S. Cohen, Postsynthetic Methods for the Functionalization of Metal-Organic Frameworks, Chemical Reviews, vol. 112, Sep. 14, 2011, pp. 970-1000.

Sumida et al., Impact of Metal and Anion Substitutions on the Hydrogen Storage Properties of M-BTT Metal-Organic Frameworks, Journal of the American Chemical Society, vol. 135, Dec. 17, 2012, pp. 1083-1091.

Meilikhov et al., Metals@MOFs-Loading MOFs with Metal Nanoparticles for Hybrid Functions, European Journal of Inorganic Chemistry, vol. 2010, No. 24, Jul. 9, 2010, pp. 3701-3714.

S. George, Atomic Layer Deposition: An Overview, Chemical Reviews, vol. 110, No. 1, Nov. 30, 2009, pp. 111-131.

R. Puurunen, Surface chemistry of atomic layer deposition: A case study for the trimethylaluminum/water process, Journal of Applied Physics, vol. 97, No. 121301, Jun. 30, 2005, pp. 1-52.

Marichy et al., Atomic Layer Deposition of Nanostructured Materials for Energy and Environmental Applications, Advanced Materials, vol. 24, Jan. 26, 2012, pp. 1017-1032.

J. Elam, Chapter 10, Coatings on High Aspect Ratio Structures, Atomic Layer Deposition of Nanostructured Materials, First Edition, Edited by Nicola Pinna and Mato Knez, Published 2012 by Wiley-VCH Verlag GmbH & Co. KGaA, Jan. 2, 2012, pp. 227-249.

Lu et al., Coking- and Sintering-Resistant Palladium Catalysts Achieved Through Atomic Layer Deposition, Science, vol. 335, Mar. 9, 2012, pp. 1205-1208.

Liu et al., Robust, Functional Nanocrystal Solids by Infilling with Atomic Layer Deposition, Nano Letters, vol. 11, Oct. 24, 2011, pp. 5349-5355.

Hamann et al., Aerogel Templated ZnO Dye-Sensitized Solar Cells, Advanced Materials, vol. 20, Apr. 9, 2008, pp. 1560-1564.

Cavka et al., A New Zirconium Inorganic Building Brick Forming Metal Organic Frameworks with Exceptional Stability, Journal of the American Chemical Society, vol. 130, Sep. 26, 2008, pp. 13850-13851.

Morris et al., Synthesis, Structure, and Metalation of Two New Highly Porous Zirconium Metal-Organic Frameworks, Inorganic Chemistry, vol. 51, Jun. 7, 2012, pp. 6443-6445.

Feng et al., Zirconium-Metalloporphyrin PCN-222: Mesoporous Metal-Organic Frameworks with Ultrahigh Stability as Biomimetic Catalysts, Angewandte Chemie Int. Ed., vol. 51, Aug. 21, 2012, pp. 10307-10310.

(56) References Cited

OTHER PUBLICATIONS

Bon et al., Zr- and Hf-Based Metal-Organic Frameworks: Tracking Down the Polymorphism, Crystal Growth & Design, vol. 13, No. 3, Feb. 14, 2013, pp. 1231-1237.

Gordon et al., A Kinetic Model for Step Coverage by Atomic Layer Deposition in Narrow Holes or Trenches, Chemical Vapor Deposition, vol. 9, No. 2, 2003, pp. 73-78.

Elam et al., Conformal Coating on Ultrahigh-Aspect-Ratio Nanopores of Anodic Alumina by Atomic Layer Deposition, Chemistry of Materials, vol. 15, No. 18, Aug. 14, 2003, pp. 3507-3517.

Valenzano et al., Disclosing the Complex Structure of UiO-66 Metal Organic Framework: A Synergic Combination of Experiment and Theory, Chemistry of Materials, vol. 23, Mar. 4, 2011, pp. 1700-1718.

Larabi et al., Titration of $Zr_3(\mu\text{-OH})$ Hydroxy Groups at the Cornerstones of Bulk MOF UiO-67, $[Zr_6O_4(OH)_4(biphenyldicarboxylate)_6]$, and Their Reaction with $[AuMe(PMe_3)]$, European Journal of Inorganic Chemistry, vol. 2012, No. 18, May 11, 2012, pp. 3014-3022.

He et al., Infrared Studies of the Adsorption of Synthesis Gas on Zirconium Dioxide, Journal of Catalysis, vol. 87, 1984, pp. 381-388.

Cui et al., Stereoselective construction of fluorinated indanone derivatives *via* a triple cascade Lewis acid-catalyzed reaction, Chemical Communications, vol. 2007, No. 22, Apr. 4, 2007, pp. 2284-2286.

Deria, P., et al., "Versatile functionalization of the NU-1000 platform by solvent-assisted ligand incorporation," *Chemical Communications*, Jan. 9, 2014, vol. 50, No. 16, 4 pp.

International Search Report and Written Opinion for Intl. Patent Appl. No. PCT/2015/014082, mailed on May 29, 2015, 11 pp.

Beyzavi, M. Hassan et al., "A hafnium-based metal organic framework as an efficient and multifunctional catalyst for facile CO2 fixation and regioselective and enantioretentive epoxide activation," *Journal of the American Chemical Society*, vol. 136, No. 45, Oct. 30, 2014 (e-pub.), pp. 15861-15864; see, also, abstract.

Furukawa, Hiroyasu et al., "The chemistry and applications of metal-organic frameworks" *Science*, vol. 341, Article No. 1230444, 2013, 12 pages; see, also, abstract.

International Search Report & Written Opinion for Intl. Patent. Appl. No. PCT/US2015/061475, mailed on Mar. 4, 2015, 15 pages.

Non-Final Office Action mailed on Feb. 12, 2016, for U.S. Appl. No. 14/333,792, 14 pages.

Stephenson, Casey J. et al., "Research update: A hafnium-based metal-organic framework as a catalyst for regioselective ring-opening of epoxides with a mild hydride source," *APL Materials*, vol. 2, No. 12, Article No. 123901, Oct. 27, 2014 (e-pub), pp. 1-5; see, also, abstract.

\* cited by examiner

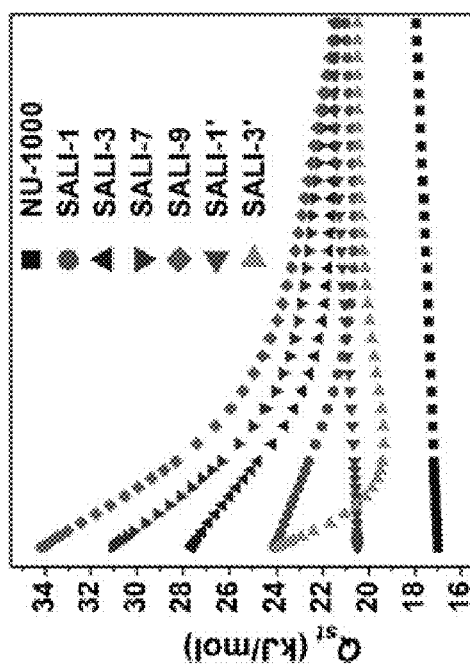
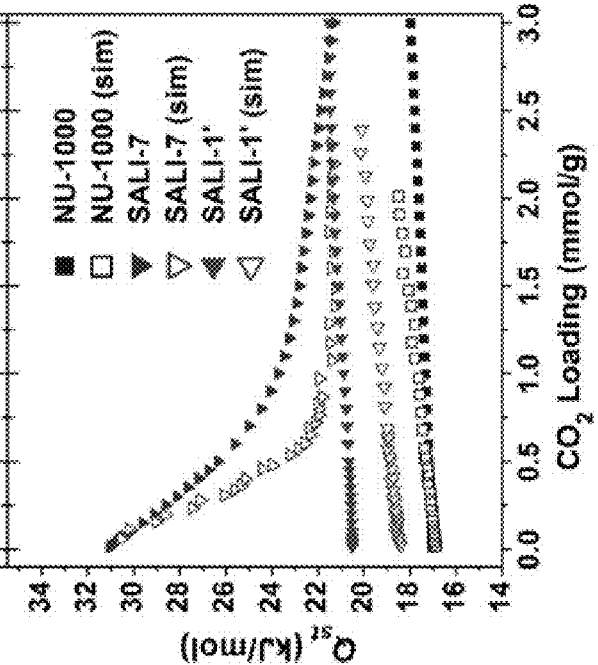
FIG. 3A
FIG. 3B

METAL-ORGANIC FRAMEWORK COMPOUNDS WITH LIGAND-FUNCTIONALIZED METAL NODES

CROSS-REFERENCE TO RELATED APPLICATIONS

The present application claims priority to U.S. Provisional Patent Application No. 61/934,981 that was filed Feb. 3, 2014, the entire contents of which are hereby incorporated by reference.

BACKGROUND

Metal-organic frameworks (MOFs) constitute a rapidly growing class of solid-state compounds. They are built up from multitopic organic linkers and metal-based nodes which are interconnected via coordination bonds. From a functional materials perspective, due to their chemical diversity and high surface area, MOFs have garnered tremendous interest for many practical applications including gas storage and separation, chemical catalysis, sensing, conductivity, and light harvesting. Given the highly modular nature of MOFs, the introduction of chemical functionality should be straightforward (at least in comparison to many other solid-state materials). Unfortunately, de novo syntheses (i.e., one-pot solvothermal syntheses) often encounter problems associated with linker solubility, linker stability, and/or the formation of undesirable structures or side products (e.g., the coordination of metal ions to the functionalized linker).

Post-synthesis incorporation of desired functionality within a given MOF structure has proven to be a key strategy in overcoming many synthetic challenges associated with de novo MOF preparation. Some of the most attractive strategies include functionalization at the metal node (via dative bonding), covalent modification of the organic linker, and solvent-assisted linker exchange (SALE) which involves exchanging one organic linker for another.

In the context of carbon capture and sequestration (CCS), fluorinated MOFs have recently emerged as attractive candidates given their hydrophobicity and the presence of X—F dipoles (where, for example, X can be C, P, Si). Hydrophobicity should render the MOF stable towards water vapor, a component in post-combustion $CO_2$ capture, while the presence of C—F dipoles should lead to favorable interactions with the quadrupole of $CO_2$ (i.e., high isosteric heats of adsorption, $Q_{st}$). For example, Eddaoudi has shown an enhancement of $CO_2$ adsorption in MOFs containing C—F dipoles in the linker; $Q_{st}^0$ values as high as 60 kJ/mol have been observed. Likewise, MOFs constructed with pyrazine and bipyridine linkers that utilize anionic hexafluorophosphate and hexafluorosilicate as pillars have demonstrated high selectivity for $CO_2$ with moderate to high $Q_{st}^0$ values (31-45 kJ/mol).

SUMMARY

Metal-organic framework compounds (MOFs) coordinated to organic ligands at their metal nodes, methods for making the ligand-coordinated MOFs and methods for using the ligand-coordinated MOFs in carbon dioxide sequestration are provided.

One embodiment of a metal-organic framework compound comprises a plurality of metal nodes coordinated by organic molecular linkers, wherein at least some of the metal nodes are coordinated to carbon-containing ligands, such as carboxylate ligands, phosphonate ligands, or a combination thereof. The carboxylate and phosphonate ligands are coordinated to the metal centers via carboxylate oxygen atoms or phosphonate oxygen atoms, respectively.

One embodiment of a method of coordinating ligands to a metal-organic framework compound that comprises a plurality of metal nodes coordinated by organic molecular linkers, wherein at least some of the metal nodes are terminated by one or more hydroxyl groups, comprises: exposing the metal-organic framework compound to a solution comprising carboxylic acid group-containing molecules, phosphonic acid group-containing molecules, or a combination thereof, under conditions at which the terminal hydroxyl groups react with the carboxylic acid groups, the phosphonic acid groups, or a combination thereof to form carboxylate ligands, phosphonate ligands, or a combination thereof, coordinated to the metal nodes.

One embodiment of a method for sequestering carbon dioxide using the ligand-coordinated metal-organic framework compounds comprises the steps of: exposing the ligand-coordinated metal organic framework compounds to an environment containing carbon dioxide molecules, wherein carbon dioxide molecules are adsorbed by the ligand-coordinated metal organic framework compounds and thereby removed from the environment.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 3(A). $Q_{st}$ of NU-1000, SALI-n and SALI-n' samples calculated from experimental isotherm data.

FIG. 3(B). $Q_{st}$ of NU-1000, SALI-n and SALI-n' samples: a comparison of simulated (sim) and experimental $Q_{st}$ values for selected MOFs.

DETAILED DESCRIPTION

Metal-organic framework compounds (MOFs) coordinated to organic ligands at their metal nodes are provided.

Also provided are methods for making the ligand-coordinated MOFs and methods for using the ligand-coordinated MOFs in carbon dioxide sequestration.

The MOFs comprise a plurality of metal nodes coordinated by organic molecular linkers that bridge the metal nodes. At least some of the metal nodes are further coordinated to carboxylate ligands, phosphonate ligands, or a combination thereof, via their carboxylate or phosphonate oxygen atoms. The ligands are distinct from the molecular linkers and, unlike the molecular linkers, they do not bridge metal nodes in the MOFs.

The ligand coordination technique used to make the MOFs, referred to as solvent assisted ligand incorporation (SALI), relies on acid-base chemistry between the hydroxyl groups on the metal nodes of a MOF and carboxylate groups and/or phosphonate groups on reactant molecules. This results in the introduction of the ligands as charge compensating and strongly bound moieties to the metal nodes via ionic bonding.

In some embodiments, the MOFs are Zr-based MOFs. MOFs comprising oxophilic $Zr^{IV}_6$ nodes are particularly useful due to their high chemical and thermal stability. An example of a mesoporous Zr-based MOF, designated NU-1000 (FIG. 1), includes an octahedral $Zr_6$ cluster capped by eight $\mu_3$-OH ligands. Eight of the twelve octahedral edges are connected to TBAPy molecular linkers ($H_4$TBAPy=1,3,6,8-tetrakis(p-benzoic-acid)pyrene), while the remaining Zr coordination sites are occupied by eight terminal —OH groups. The resultant MOF has the molecular formula $Zr_6(\mu_3\text{-OH})_8(\text{—OH})_8(\text{TBAPy})_2$ and contains mesoporous channels lined with terminal —OH ligands (~20-25% of the mesoporous channels contain a secondary structural element), which are attractive for introducing new functionality. In some such MOFs, some of the terminal hydroxyl groups may be replaced with oxo and/or aquo groups.

In some embodiments, the carboxylate and/or phosphonate ligands comprise alkyl groups and/or aryl groups (including alkyl aryl groups), bound directly or indirectly to the carboxylate or phosphonate group. The alkyl and/or aryl groups may be fluorinated. The coordination of perfluoroalkane carboxylate ligands, such as $C_1$-$C_9$ perfluoroalkane carboxylate ligands, to the metal nodes of a MOF is illustrated in Example 1. However, many other types of carboxylate and phosphonate ligands can be coordinated with the MOFs, as illustrated in Examples 2 and 3.

Figure 1:
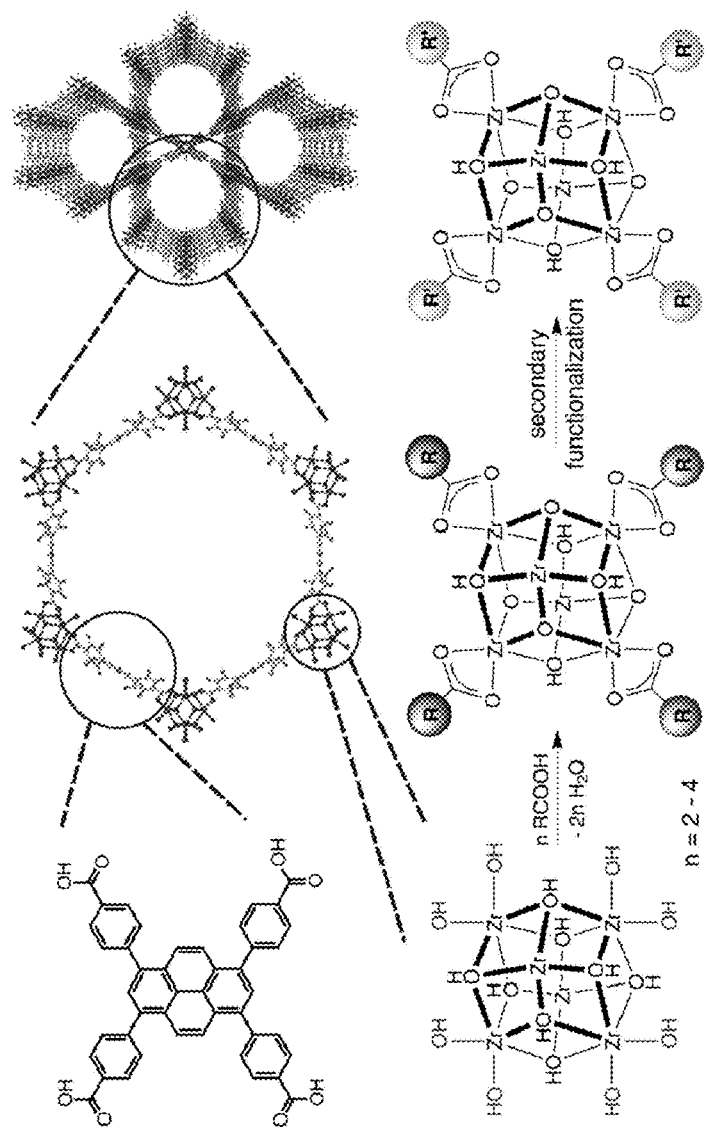
FIG. 1. Molecular representations of NU-1000 and the primary carboxylate-based Solvent-Assisted Ligand Incorporation (SALI) of the NU-1000, followed secondary functionalization.
Figure 2:
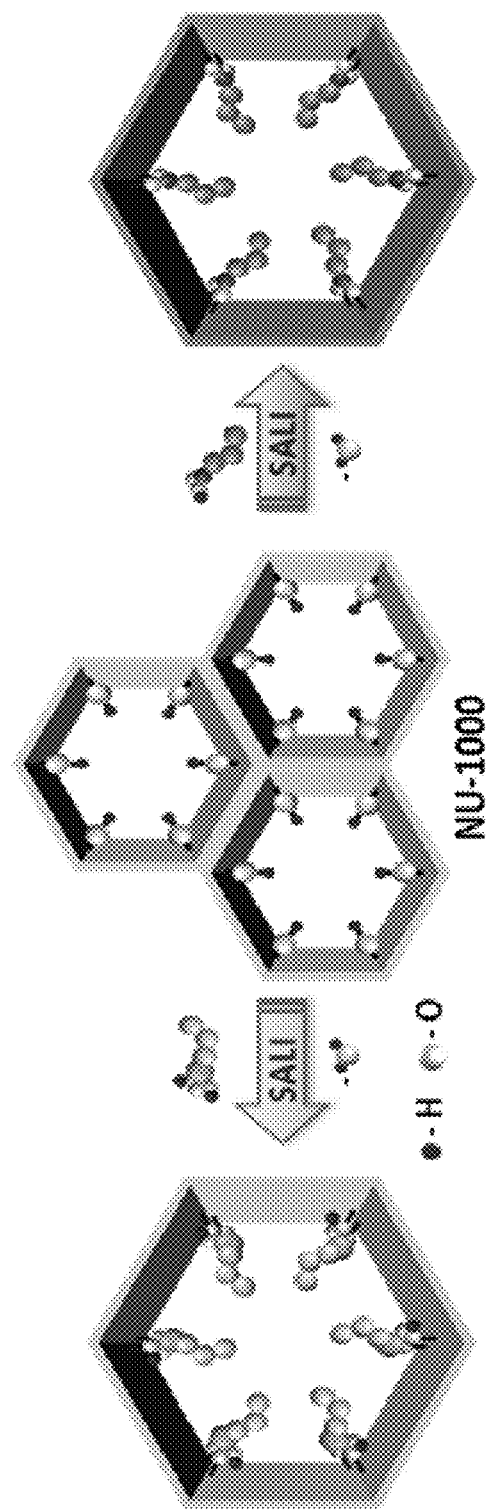
FIG. 2. Schematic illustration of SALI using an aryl phosphonate ligand (left) and a fluorinated carboxylate ligand (right).

Methods of functionalizing MOFs with the ligands are carried out on MOFs comprising a plurality of metal nodes coordinated by organic molecular linkers, wherein at least some of the metal nodes are terminated by one or more hydroxyl groups. In the methods, which are illustrated in FIGS. 1 and 2, the metal-organic framework compounds are exposed to a solution comprising carboxylic acid group-containing molecules and/or phosphonic acid group-containing molecules in an organic solvent under conditions that promote the terminal hydroxyl groups to react with the carboxylic acid groups and/or phosphonic acid groups to form carboxylate and/or phosphonate ligands coordinated to the metal nodes. Optionally, the resulting ligand-coordinated MOFs, which may be referred to as primary coordinated MOFs, can be subjected to a second reaction in which the initial ligands are reacted with a secondary reactant molecule to form secondary carboxylate or phosphonate ligand bonded to the metal nodes. Secondary reactions are illustrated in Example 2.

In some embodiments of the methods, the MOFs are coordinated to both carboxylate and phosphonate ligands. In these methods, the uncoordinated MOFs can be exposed to carboxylic acid group-containing molecules and phosphonic acid group-containing molecules simultaneously or sequentially. However, it may be desirable to coordinate the MOFs to the phosphonate ligands first, since those ligands undergo a stronger interaction with oxophilic metal ions in the nodes than do carboxylate ligands and, therefore, resist displacement by carboxylate ligands that are coordinated in a subsequent step.

The ligand coordinated MOFs can be used in methods of sequestering carbon dioxide. In these methods, the ligand-coordinated MOFs are exposed to an environment containing carbon dioxide molecules. Carbon dioxide molecules are then adsorbed by the metal organic framework compounds and, thereby, removed from the environment. The adsorbed carbon dioxide molecules can then be removed from the ligand-coordinated MOFs.

Example 1

This example illustrates the use of SALI to efficiently attach perfluoroalkane-carboxylates of various chain lengths ($C_1$-$C_9$) on the $Zr_6$ nodes of NU-1000. These fluoroalkane functionalized mesoporous MOFs, termed herein, SALI-n were studied experimentally and theoretically as potential $CO_2$ capture materials.

Figure 5:
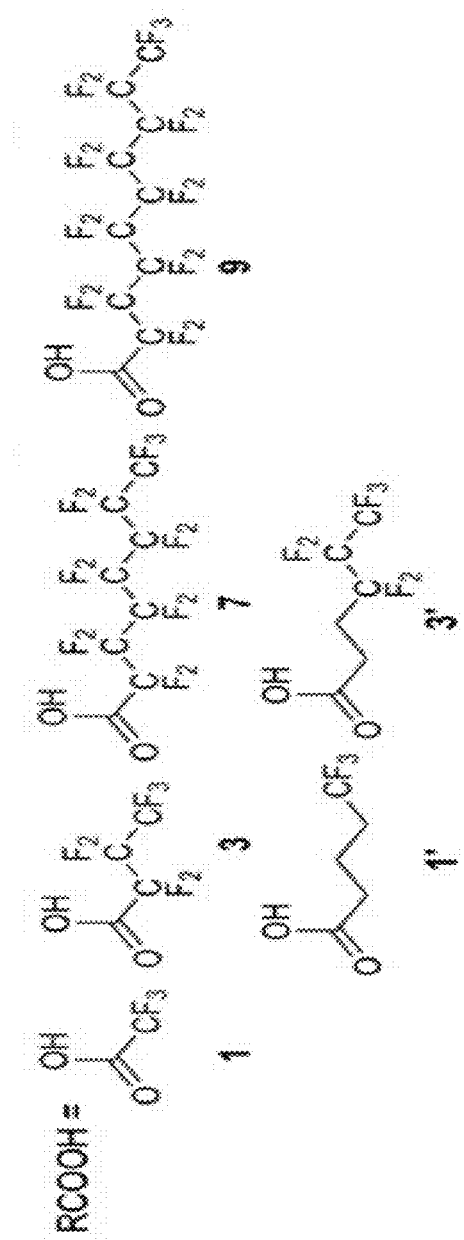
FIG. 5. Carboxylic acid ligands for use in SALI.

To the inventors' knowledge, no study has systematically investigated the effects of alkyl C—F dipole on $CO_2$ adsorption. Hence $[Zr_6\mu_3\text{-OH})_8(\text{—OH})_8]^{8+}$ node of NU-1000, functioning as a platform for SALI, was utilized to introduce perfluoroalkane functionality within its mesoporous channels. Perfluoroalkyl carboxylic acids of varying chain length (1, 3, 7 and 9; FIG. 5) were utilized. Likewise fluoroalkanes bonded to the carboxylic acids via ethylene ($CH_2$—$CH_2$) and propylene ($CH_2$—$CH_2$—$CH_2$) moieties were utilized to better understand any cooperative $CO_2$ adsorption effects between the perfluoroalkanes and the $Zr_6$ node. Unlike previous metal node functionalization strategies, which utilize dative bonding to coordinatively unsaturated metal sites, SALI relies on acid-base chemistry between the hydroxyl groups on the NU-1000 node and the carboxylate group of the perfluorinated chain. This results in the introduction of functional groups as charge compensating and strongly bound moieties to the NU-1000 node via ionic bonding. Furthermore, while the nodes of Zr-based MOFs have previously been functionalized with various metals, the inventors believe this is the first example utilizing the node to introduce carbon-based functionality.

A brief description of the materials and methods used in this example is provided here. For more detail, see the "Detailed Materials and Methods" section below. To start, a microcrystalline powder of NU-1000 was synthesized and exposed to a 0.1 M solution of fluoroalkyl carboxylic acid (i.e., 8 equiv per $Zr_6$ node) in DMF at 60° C. for 18-24 h. A description of the synthesis of the NU-1000 can be found in Mondloch, J. E.; Bury, W.; Fairen-Jimenez, D.; Kwon, S.; DeMarco, E. J.; Weston, M. H.; Sarjeant, A. A.; Nguyen, S. T.; Stair, P. C.; Snurr, R. Q.; Farha, O. K.; Hupp, J. T. J. Am. Chem. Soc. 2013, 135, 10294 (Mondloch et al.). The degree of functionalization was quantified by $^1$H and $^{19}$F NMR after decomposing the samples in a 10% $D_2SO_4$/DMSO-$d_6$ mixture; the $^{19}$F signals of the perfluoroalkanes (1, 3, 7, and 9; FIG. 5) were integrated against the $^1$H NMR signals of the TBAPy ligand using an internal standard (2,5-dibromo-1,4-bis(trifluoromethyl) benzene). Approximately 3.4-4 perflouroalkyl carboxylates, per $Zr_6$ node, could be incorporated within NU-1000 (Table 1). (Complete functionalization considering the SALI stoichiometry shown in FIG. 1, is four carboxylates per $Zr_6$ node). The resultant materials were termed SALI-n (e.g. SALI-1-SALI-9), where n is the carboxylic acid ligand. To ensure the maximum accessibility of the $Zr_6$ node by these carboxylates, SALI experiments were carried out at higher temperature (80° C.) and longer times (36 h). The degree of functionalization for these extended exposures was the same as those at lower temperature and shorter time (i.e., ~4 fluorocarboxylates per $Zr_6$ cluster).

Powder X-ray diffraction (PXRD) measurements confirmed that the functionalized samples retained their crystallinity. There was a change in relative intensities of the peaks that appeared at two-theta values of 2.5, 4.5 and 5 upon functionalization. Going from a shorter to longer alkyl chain (e.g. SALI-1 to SALI-9) the intensity of the peak at two-theta=4.5 increased; this change was similar to those observed previously for samples of NU-1000 metallated at the node. (See, Mondloch et al.) The results can be explained by functionalization occurring at the $[Zr_6(\mu_3\text{-OH})_8(\text{—OH})]^{8+}$ node of NU-1000 (i.e., increased electron density about the 010 plane where a significant portion of the $Zr_6$ node is sited).

Further evidence consistent with functionalization at the node was provided by the results of diffuse reflectance infrared Fourier transform spectroscopy (DRIFTS) measurements. A peak appeared at 3674 cm$^{-1}$ which was assigned to terminal —OH groups while a shoulder at 3671 cm$^{-1}$ was consistent with the bridging $\mu_3$-OH groups observed for UiO-66.[22] For SALI-1, SALI-3, and SALI-7, clear disappearance of a sharp peak at 3674 cm$^{-1}$ indicated that only the terminal —OH sites were occupied by the fluoroalkyl carboxylates in these functionalized samples, where the peak for the remaining bridging —OH ligands could be discerned at 3671 cm$^{-1}$. Given that functionalization on the $Zr_6$ node by four carboxylates caused spectral disappearance of all eight terminal —OH ligands, it was postulated that the local coordination environment of the nodes of SALI-n functionalization is similar to that of UiO-66. Thus, the added carboxylate ligands in SALI-n compounds coordinate to each of the four equatorial $Zr^{IV}$ ions as bidentate ligands, with a resultant molecular formula $Zr_6(\mu_3\text{-O})_4(\mu_3\text{-OH})_4(CO_2^-)_{12}$. Functionalization of NU-1000 with four fluoroalkyl carboxylates involves net removal of eight water molecules (FIG. 1). Notably, the DRIFTS spectrum of SALI-1 was identical to that of the as-synthesized form of NU-1000, where in addition to linkers, the $Zr_6$ cluster of this form features four chelating benzoates (residual modulators). (See, Mondloch et al.)

The $N_2$ adsorption isotherms of the fluoroalkane functionalized SALI-n samples retained the type IVc shape found for the parent NU-1000. Brunauer-Emmett-Teller (BET) analyses of the isotherms indicated a systematic decrease in surface area from 2320 m$^2$ g$^{-1}$ for NU-1000 to 1710 and 870 for SALI-1 and SALI-9. As expected, the gravimetric and volumetric surface areas, along with pore sizes and pore volumes decreased as a function of chain length. The $CO_2$ adsorption isotherm for NU-1000 showed Langmuir type behavior with an uptake of 31 cc/cc at 1 bar (T=273 K). In contrast, the $CO_2$ adsorption profiles for all the SALI-n derivatives showed a steeper uptake in the isotherm resulting, generally, in higher volumetric uptake (Table 1) at low-pressure (~0.15 bar; relevant for $CO_2$ sequestration).

TABLE 1

BET Surface Areas, Pore diameters, Pore Volumes, $CO_2$ uptake and $Qst^0$ for SALI-n samples, and NU-1000.

| MOF | Ligand | Ligand:$Zr_6$ | BET Surface Area (m$^2$ g$^{-1}$) | BJH Pore diameter (Å) | Pore Volume (cc/g) | $CO_2$ uptake @ 0.15 bar (cc/cc)$^c$ | $Qst^0$ (kJ/mol) |
|---|---|---|---|---|---|---|---|
| NU-1000 | | | 2320 | 31 | 1.4 | 5.6 | 17 |
| SALI-1 | $CF_3CO_2^-$ | 4 | 1710 | 30 | 1 | 9.4 | 24 |
| SALI-3 | $CF_3(CF_2)_2CO_2^-$ | 3.8 | 1410 | 30 | 0.8 | 8.8 | 28 |
| SALI-7 | $CF_3(CF_2)_6CO_2^-$ | 3.7 | 900 | 28 | 0.6 | 7.2 | 31 |
| SALI-9 | $CF_3(CF_2)_8CO_2^-$ | 3.4 | 870 | 28 | 0.6 | 6.2 | 34 |
| SALI-1' | $CF_3(CH_2)_3CO_2^-$ | 2 | 1600 | 30 | 1 | 6.4 | 21 |
| SALI-3' | $CF_3(CF_2)_2(CH_2)_2CO_2^-$ | 3 | 1400 | 30 | 0.9 | 5.3 | 24 |

$^c$T = 273 K

In order to estimate the average binding energy of $CO_2$ to the perfluoroalkane-modified samples, isotherms collected at different temperatures were analyzed. Briefly, single-site or dual-site Langmuir models followed by Clausius-Clapeyron analysis were utilized to extract loading-dependent values of $Q_{st}$ for each compound (Table 1). In the zero-uptake limit ($Q_{st}^0$), all SALI-n samples showed a higher value than unmodified NU-1000, with the value systematically increasing with fluoroalkane chain length. The value of $Q_{st}^0$ for SALI-9 was twice that for unmodified NU-1000. The $Q_{st}$ plots for all SALI-n samples showed a decrease to ~21 kJ/mol, which corresponds to the heat of adsorption for the weaker binding sites at higher $CO_2$ loading. For SALI-1 and SALI-9, the $Q_{st}$ plateaus at a loading of 1.5 and 1.0 mmol/g of MOF respectively; these correspond to ~1$CO_2$ per fluoroalkane chain. Note that the $Q_{st}$ values for the SALI-n samples were higher than the enthalpy of liquefaction for $CO_2$ (17 kJ/mol) and similar to the $Q_{st}$ for MOFs with open metal sites such as Co-MOF-74 and HKUST-1. (See, Wang, Q. M.; Shen, D.; Bülow, M.; Lau, M. L.; Deng, S.; Fitch, F. R.; Lemcoff, N. O.; Semanscin, J. Microporous Mesoporous Mater. 2002, 55, 217.) To detect possible synergistic effects due to the zirconium-oxo node contributing to the CF—$CO_2$ interaction, SALI-1' and SALI-3' were studied. Here the fluoroalkane chains are bonded to the carboxylate functionality via an ethylene or propylene moiety (FIG. 1). The $Q_{st}^0$ values for both of these SALI-n' samples were ~3-4 kJ/mol lower than their corresponding perfluoroalkyl counterparts. Additionally, the $Q_{st}$ plot of SALI-1', as a function of $CO_2$ loading was similar to that of the unmodified NU-1000 sample, with the exception of slightly higher $Q_{st}$.

Figure 4:
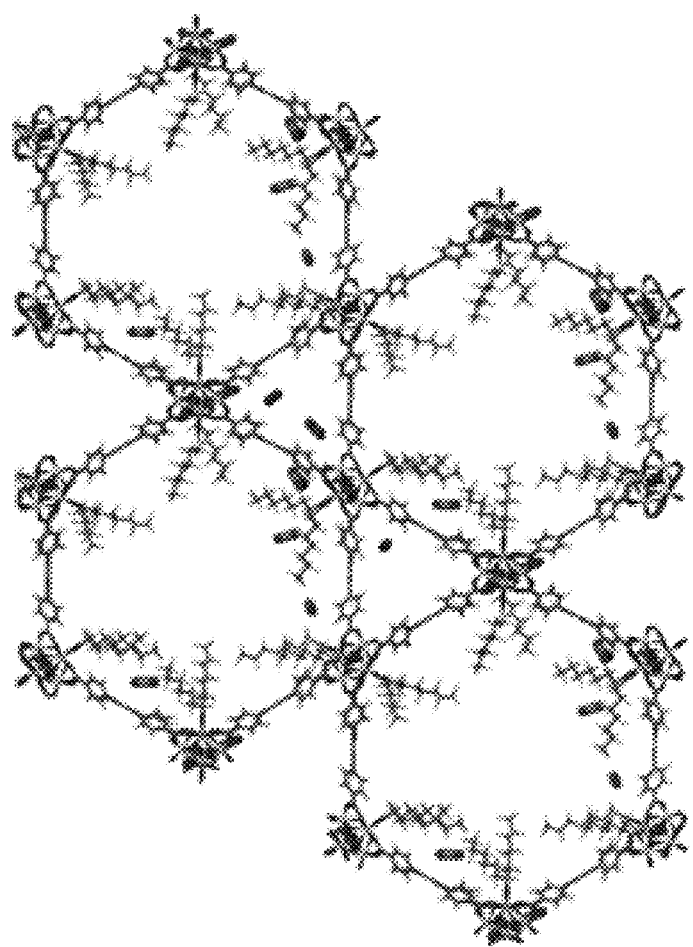
FIG. 4. Simulated snapshot of $CO_2$ adsorption depicting the primary $CO_2$ binding sites in SALI-7 (T=293 K and P=0.1 bar).

Theoretical modeling confirmed the experimental observations: (1) the simulated $Q_{st}$ for respective model MOFs were in good agreement with the experimental data and (2) primary $C_{O2}$ binding sites were close to the $Z_{r6}$ nodes (FIG. 1). $Q_{st}$ of NU-1000, SALI-n and SALI-n' samples: calculated from experimental isotherm data; and a comparison of simulated (sim) and experimental $Q_{st}$ values for selected MOFs are shown in FIGS. 3(A) and 3(B), respectively. Though the ideal adsorbed solution theory (IAST) (see, Myers, A. L.; Prausnitz, J. M. AIChE J. 1965, 11, 121) calculated selectivity for the $CO_2$ adsorption over $N_2$ ($CO_2$/$N_2$:10:90) was low in these mesoporous MOF structures, preference for $CO_2$ adsorption increased in the long perfluoroalkyl functionalized SALI-9 compared to the non-functionalized NU-1000. Water adsorption data indicate only modest enhancement in hydrophobicity upon perfluoroalkane functionalization. A simulated snapshot of $CO_2$ adsorption depicting the primary $CO_2$ binding sites in SALI-7 is provided in FIG. 4.

In conclusion, an efficient functionalization synthesis method for $Z_{r6}$-based mesoporous MOFs based on solvent assisted ligand incorporation (SALI) has been developed. Spectroscopic data indicate that these carboxylates are bound to the $Z_{r6}$ node, resulting in a UiO-66 type metal node, $Zr_6(\mu_3-OH)_4(\mu_3-O)_4(CO^{2-})_{12}$. $CO_2$ adsorption studies indicated that perfluoroalkane functionalized nodes in the SALI-n system synergistically act as the primary $CO_2$ binding sites manifesting in systematically higher values for $Q_{st}$ with increasing in chain length. SALI is attractive for enhancing chemical competency and functionality within MOFs for a wide variety of applications, including catalysis, sorption, and separations.

Detailed Materials and Methods for Example 1

Materials

Reagents and Solvents:

Acetone (Macron, 98%), chloroform (BDH, 99.8%), 1,4-dioxane (Aldrich, 99.8%, anhydrous), N,N'-dimethylformamide (DMF) (Macron, 99.8%), diethylether (Aldrich, 99.0%), deuterated chloroform (d-$CDCl_3$) (Cambridge, 99.8%), deuterated dimethylsulfoxide ($d_6$-DMSO) (Cambridge, 99%), deuterated sulfuric acid ($D_2SO_4$) (Cambridge, 96-98% solution in $D_2O$) were used as received without further purification. Perfluoroalkyl and fluoroalkyl carboxylic acids were purchased from Synquest lab and used as received.

Synthesis of NU-1000 in DMF:

Microcystalline NU-1000 was prepared via solvothermal method according to the published procedure except slight modification. (See Mondloch et al.)

70 mg of anhydrous $ZrCl_4$ (0.30 mmol) and 2700 mg (22 mmol) of benzoic acid were mixed in 8 mL of DMF (in a 6-dram vial) and ultrasonically dissolved. The clear solution was incubated in an oven at 80° C. for 1 h. After cooling down to room temperature 40 mg (0.06 mmol) of $H_4$TBAPy was added to this solution and the mixture was sonicated for 20 min. The yellow suspension was heated in an oven at 120° C. for 48 h. After cooling down to ~50° C. the supernatant solution was decanted, yellow polycrystalline material was isolated by filtration (35 mg of activated material, 54% yield) and soaked in DMF for 8 h at room temperature and finally washed with fresh DMF. This material was activated with HCl.

Activation Procedure for NU-1000:

As synthesized NU-1000 was activated using a slightly modified method previously reported. (See Mondloch et al. and Feng, D.; Gu, Z.-Y.; Li, J.-R.; Jiang, H.-L.; Wei, Z.; Zhou, H.-C. Angew. Chem. Int. Ed. 2012, 51, 10307.) Approximately 40 mg of solvated ("wet") material was soaked in 12 ml of DMF and 0.5 ml of 8 M aqueous HCl was added. This mixture was heated in an oven at 100° C. for 24 h. After cooling to ~50° C. the supernatant solution was decanted and the material was soaked in DMF for 12 h and subsequently washed twice with DMF to remove HCl impurities. The solid residue was then soaked in acetone for 12 h, washed twice with acetone and soaked in acetone for additional 12 h. NU-1000 was filtered, briefly dried on a filter paper and activated at 120° C. under vacuum for 12 h on the preparation station of ASAP 2020 instrument. Characteristic $^1$H NMR, $N_2$ adsorption isotherms, and DRIFTS data are consistent with the removal of benzoic acid from the $Zr_6$ node and the incorporation of —OH groups as reported in the previous publication. (See Mondloch et al.)

Secondary Structural Element:

It is important to note that ~20-25% of the mesoporous channels of the NU-1000 contain a secondary structural element. Modeling of the secondary element as $[Zr_6(\mu_3-O)_4(\mu_3-OH)_4]_2(TBAPy)_6$ which connects to 12 $Zr_6$ nodes of the parent framework through six TBAPy ligands provided.

Instrumentation.

$^1$H NMR spectra were recorded on a 500 MHz Varian NOVA spectrometer and referenced to the residual solvent peak. Powder X-ray diffraction measurements were carried out on a Bruker M IμS microsource with Cu Kα radiation and an Apex II CCD detector. The samples were mounted in capillaries as powders, sealed with wax and placed on a goniometer head. The data were collected on an area detector with rotation frames over 180° in φ and at 2θ values of 12, 24, and 36° being exposed for 10 min at each frame. Overlapping sections of data were matched, and the resulting pattern was integrated using Broker's APEX2 phase ID program. The powder patterns were treated for amorphous background scatter. Diffuse reflectance infrared spectra (DRIFTS) were recorded on a Nicolet 7600 FTIR spectrometer equipped with an MCT detector. The spectra were collected in a KBr mixture under $N_2$ purge (samples prepared in atmosphere); KBr was utilized as the background. $N_2$ adsorption isotherms were collected on ASAP 2020 (Micromeritics). All pore size distributions were obtained using the BJH method on the desorption branch of the $N_2$ isotherms. $CO_2$ adsorption isotherms were collected on IGA-200 (Hiden Isochema)

Synthesis of SALI-n from NU-1000 ($Zr_6(\mu_3-OH)_8(OH)_8(TBAPy)_2$).

Figure 8:
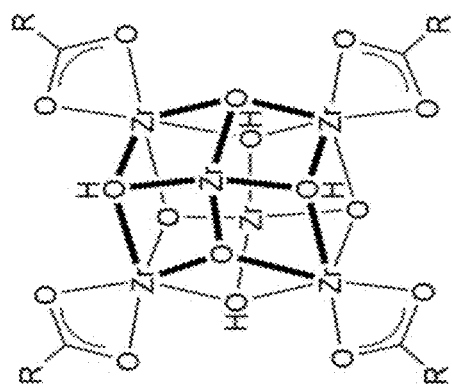
FIG. 8. Synthesis of SALI-n from NU-1000.
Figure 8:
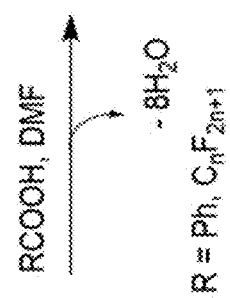
Figure 8:
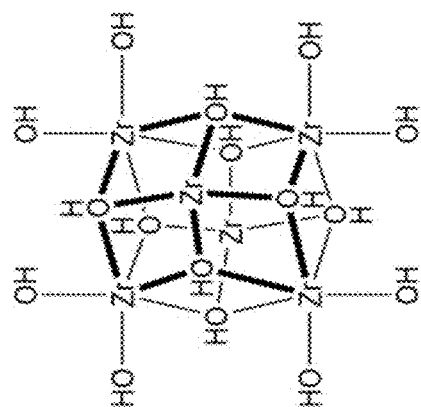

A 60 mg portion of activated NU-1000 (0.027 mmol) was loaded in a 2 mL microwave vial (Biotage). Subsequently a 2.4 mL of 0.1M solution of fluoroalkane carboxylic acid (0.24 mmol) in DMF was added to the reaction vial, which was then sealed and heated at 60° C. for 18-24 h with occasional swirling. The supernatant of the reaction mixture was decanted and the MOF sample was soaked into fresh hot DMF which was then filtered, washed sequentially with DMF, acetone and ether (60, 40 and 30 mL each), and finally air dried. The synthesis is shown in FIG. 8.

Synthesis of SALI-1 from as Synthesized, NU-1000/BA.

Figure 9:
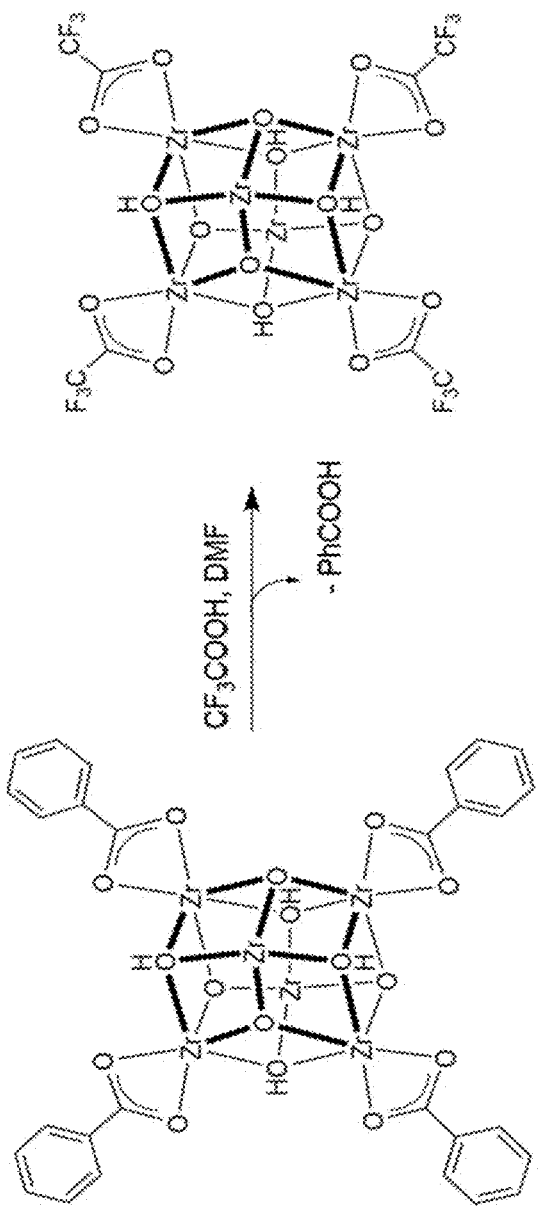
FIG. 9. Synthesis of SALI-n from NU-1000/BA.

As-synthesized NU-1000 contains benzoate ligands (here after referred as NU-1000/BA) present on the $Zr_6$ nodes (4 benzoates are present per node) and the DRIFTS spectra are identical to that of SALI-1. When NU-1000/BA (30 mg) was exposed to trifluoroacetic acid (0.11 mmol) in DMF (1.2 mL) at 60° C., benzoate ligands on the $Zr_6$ node were replace by trifluoroacetate, to produce SALI-1 via a ligand exchange process, which relies on a weaker benzoic acid (pKa~4.2) being replaced by a stronger perfluoroalkyl carboxylic acid (pKa~0.23). The synthesis is shown in FIG. 9. Formation of SALI-1 was confirmed via $^1$H, $^{19}$F NMR spectra. However, this ligand replacement process was not universal for respective SALI-n' samples.

Activation Procedure for NU-1000 and SALI-n for Gas Sorption Measurements.

SALI-n and SALI-n' samples were activated at 120° C. under vacuum for 12 h. $^1$H, $^{19}$F NMR, PXRD, N$_2$ adsorption measurements, and DRIFTS data were consistent with the removal of —OH groups from the Zr$_6$ node and the incorporation of perfluoroalkyl carboxylate ligands.

$^1$H and $^{19}$F NMR of SALI-n.

Functionalization of NU-1000 with perfluoroalkyl carboxylates was quantified by $^1$H and $^{19}$F NMR after decomposing the samples in a 10% D$_2$SO$_4$/DMSO-d$_6$ mixture; the $^{19}$F signals of the perfluoroalkanes (1, 3, 7, and 9; FIG. 5) were integrated against the $^1$H NMR signals of TBAPy ligand using an internal standard (2,5-dibromo-1,4-bis(trifluoromethyl)benzene.

Expected SALI Stoichiometry.

Considering ~20-25% occupancy of secondary structural elements [Zr$_6$($\mu_3$-O)$_4$($\mu_3$-OH)$_4$]$_2$(TBAPy)$_6$ in the mesoporous channels of the NU-1000, SALI stoichiometry was estimated to be 3.2 carboxylates per Zr$_6$ nodes, whereas a 0% occupance of such secondary structural elements would provide 4 carboxylates per Zr$_6$ nodes. However, considering ~20-25% occupancy of a secondary framework that is disordered about the six-fold axis running through the middle of a mesoporous channel, 4 carboxylates per Zr$_6$ nodes are expected as the SALI stiochiometry. Given that the SALI stoichiometry found for the majority of the fluoroalkyl incorporated NU-1000 was close to 4 carboxylates per Zr$_6$ nodes (3.4 for SALI-9 to a maximum of 4 for SALI-1), the secondary structural element may be a framework disordered about the six-fold axis running through the middle of a mesoporous channel.

DRIFTS Data.

DRIFTS data of NU-1000, SALI-n and SALI-n' samples were collected in a KBr mixture. A peak at 3674 cm$^{-1}$, assigned to the terminal —OH groups on the Zr$_6$ node in parent NU-1000, completely disappeared in SALI-3 and SALI-7 which underwent complete functionalization (based on the $^1$H NMR data: 3.8 carboxylate ligands per Zr$_6$ node). On the contrary, in SALI-9, SALI-1' and SALI-3', the terminal —OH stretch intensity was only partly reduced along with slight upshifts as a function of respective degree of carboxylate incorporation (3.4, 2 and 3 carboxylates were incorporated in SALI-9, SALI-1' and SALI-3' samples). A lower energy peak at 3662-3665 cm$^{-1}$ was assigned to the H-bonded species on the Zr$_6$ nodes in the functionalized materials.

SALI-7 and SALI-1' Structure Modeling.

Due to difficulties in obtaining crystals of suitable quality for single crystal analysis, the structures of SALI-7 and SALI-1' were modeled ab initio by applying a procedure based on molecular mechanics energy minimizations explained previously. (See, (a) Fairen-Jimenez, D.; Colon, Y. J.; O. K., F.; Bae, Y. S.; Hupp, J. T.; Snurr, R. Q. *Chem. Commun.* 2012, 48, 10496; (b) Farha, O. K.; Yazaydm, A. Ö.; Eryazici, I.; Malliakas, C. D.; Hauser, B. G.; Kanatzidis, M. G.; Nguyen, S. T.; Snurr, R. Q.; Hupp, J. T. *Nature Chem.* 2010, 2, 944; (c) Strutt, N. L.; Fairen-Jimenez, D.; Iehl, J.; Lalonde, M. B.; Snurr, R. Q.; Farha, O. K.; Hupp, J. T.; Stoddart, J. F. *J. Am. Chem. Soc.* 2012, 134, 17436.)

Figure 11:
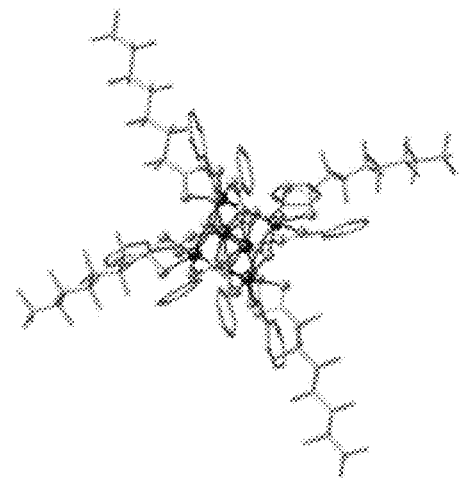
FIG. 11. Atomistic representation of $C_7F_{15}COO$-functionalized $Zr_6$ node of SALI-7 (only the phenyl-carboxylates of the 1,3,6,8-tetrakis(p-benzoic-acid)pyrene (TBAPy) linkers are shown for clarity; also hydrogen atoms were removed for clarity).
Figure 10:
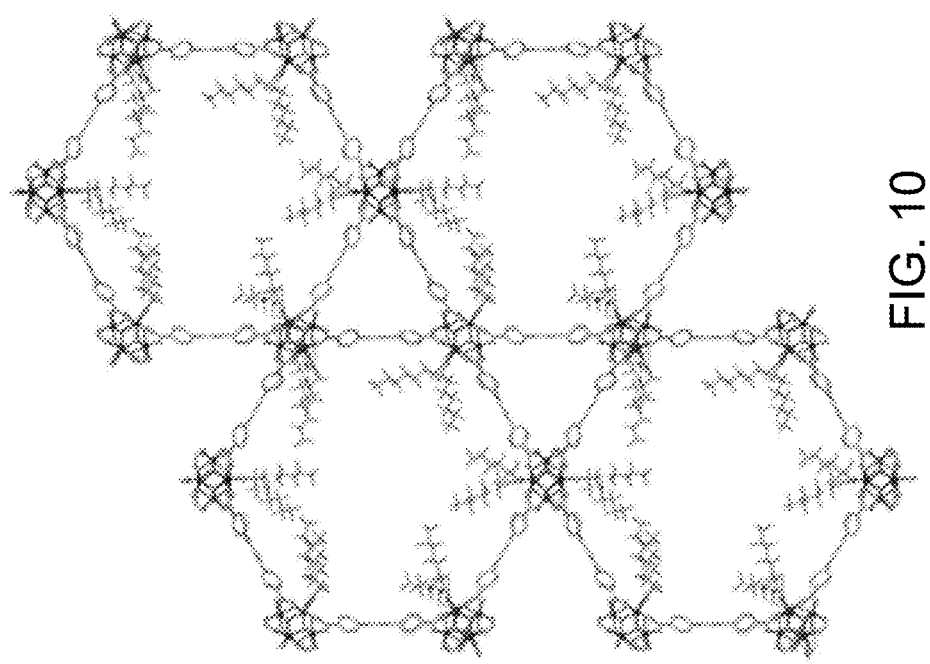
FIG. 10. Atomistic representations of SALI-7.

A description of the NU-1000 ab initio structure modeling and the crystallographic structure solution were presented in Mondloch et al. For this work, the initial coordinates of NU-1000 were taken from the Crystallographic Information File reported in that prior publication. Starting with these coordinates, SALI-1' was built by adding the ab-initio optimized fluoroalkyl chains to the Zr$_6$ nodes in silico. Four C$_7$F$_{15}$COOH (7) or CF$_3$C$_3$H$_6$COOH (1') chains were attached to each Zr$_6$ node. The new carboxylate ligands coordinate to each equatorial Zr$^{IV}$ as a bidentate ligand via two carboxylate oxygen atoms, and the resulting molecular formula is Zr$_6$($\mu_3$-O)$_4$($\mu_3$-OH)$_4$(CO$_2$)$_{12}$. Similar to the UiO-66 node, this newly functionalized Zr$_6$ node provides a structure where the fluoroalkyl chains protrude into the mesoporous hexagonal channel of the NU-1000. Thereafter, the structures were subject to geometry optimization based on molecular mechanics calculations by modifying all the atomic positions. These calculations were performed with the Forcite module of Materials Studio using an algorithm that is a cascade of the steepest descent, adjusted basis set Newton-Raphson, and quasi-Newton methods. (Accelrys Software Inc: San Diego, Calif. 92121, USA.) Bonded and non-bonded interactions were treated using the Universal Force Field (UFF). (Rappé, A. K.; Casewit, C. J.; Colwell, K. S.; Goddard, W. A.; Skiff, W. M. *J. Am. Chem. Soc.* 1992, 114, 10024.) A cutoff distance of 12.8 Å was used for the Lennard-Jones interactions. The long-range electrostatic interactions arising from the presence of partial atomic charges were modeled using a Coulombic term using the Ewald method. Partial atomic charges for the NU-1000 framework atoms were derived from the extended charge equilibration method (EQeq) using an in-house written code, and the charges for the C$_7$F$_{15}$COOH (7) and CF$_3$(CH$_2$)$_3$COOH (1') atoms were taken from OPLS. (See, Wilmer, C. E.; Kim, K. C.; Snurr, R. Q. *J. Phys. Chem. Lett.* 2012, 3, 2506; and Watkins, K.; Jorgensen, W. L. *J. Phys. Chem. A* 2001, 105, 4118.) The structures of SALI-7 and the C$_7$F$_{15}$COO-functionalized Zr$_6$ node are shown in FIGS. 10 and 11, respectively.

Experimental N$_2$ Adsorption Isotherm Analysis.

For all isotherm analyses, the consistency criteria described by Rouquerol et al. and Walton et al. were satisfied. (See, Rouquerol, J.; Llewellyn, P.; Rouquerol, F. *Stud. Surf. Sci. Catal.* 2007, 160, 49; and Walton, K. S.; Snurr, R. Q. *J. Am. Chem. Soc.* 2007, 129, 8552.)

Volumetric Experimental N$_2$ Isotherms and Pore Size Distributions for NU-1000, SALI-1, and SALI-n'.

Volumetric N$_2$ isotherms were calculated by using the carboxylic acid loading, determined by $^1$H NMR and $^{19}$F NMR, in Table 1. It was assumed that one R—COO moiety was bound to each of the four equatorial Zr$^{IV}$ of the Zr$_6$ nodes and that two water molecules were removed. A crystallographically predicted density of 0.49 cc/g was used for NU-1000 and estimated densities of 0.56 cc/g for SALI-1, 0.64 cc/g for SALI-3, 0.81 cc/g for SALI-7, 0.85 cc/g for SALI-9, 0.54 cc/g for SALI-1', and 0.62 cc/g for SALI-3' were used, based on simple molecular formula calculations.

Pore Volume in SALI-n Considering the Volume Occupied by the Fluoroalkyl Chains.

As described in Table 1, the pore volume systematically decreased in SALI-n relative to that of NU-1000 with increasing fluoroalkyl chain length. Utilizing the SALI stoichiometry for each SALI-n sample obtained from the $^1$H NMR data (Table 1), it was estimated that 0.18, 0.28, 0.42, and 0.46 g of fluoroalkyl carboxylates were present per gram of SALI-1, SALI-3, SALI-7 and SALI-9 materials, respectively; this corresponds to their liquid-phase volumes of 0.12, 0.17, 0.25, 0.27 cc per g of their respective MOF samples. Note that the reductions in the respective pore volumes from the parent NU-1000, as measured from the N$_2$ isotherm at 77 K, are 0.4, 0.6, 0.8 and 0.8 cc/g Experimental CO$_2$ Adsorption Isotherm Analysis and Comparison with Simulated CO$_2$ Adsorption Isotherms.

Experimental CO$_2$ isotherms for all MOF samples were measured gravimetrically at three temperatures (273 K, 283 K, and 298 K). Volumetric CO$_2$ isotherms were calculated using the density for each sample used in calculating the volumetric N$_2$ isotherm.

CO$_2$ Adsorption Selectivity in NU-1000 and SALI-9 for CO$_2$/N$_2$ Gas Mixtures Calculated from Ideal Adsorbed Solution Theory.

Ideal Adsorbed Solution Theory (IAST) was applied to estimate the selectivity for CO$_2$/N$_2$ mixed-gas adsorption in two representing MOF structures, NU-1000 and SALI-9. Pure component isotherms of N$_2$ and CO$_2$ from experiment were used to calculate the selectivity of CO$_2$ over N$_2$ for a gas phase composition of CO$_2$/N$_2$=10:90. (See, Myers, A. L.; Prausnitz, J. M. AlChE J. 1965, 11, 121.)

Experimental Water Adsorption Isotherms and Water Stability.

Water adsorption isotherms of the NU-1000, and SALI-n samples were recorded at 298 K at 1 bar using helium as carrier gas. Compared to the parent NU-1000, all the SALI-n samples showed systematic lower gravimetric uptake with increasing CF$_n$ chain length. These water adsorption data indicated only very mild enhancement in hydrophobicity upon perfluoroalkane functionalization. Congruent with their pore volumes (Table 1), all the SALI-n samples showed systematically lower water uptake with increasing chain length.

Example 2

This example explores the chemical generality and group tolerance of the SALI approach using NU-1000 as a modification platform. Additionally it shows that the large cavities and chemical robustness of the parent framework permit newly installed functional groups to be further chemically derivatized.

Figure 6:
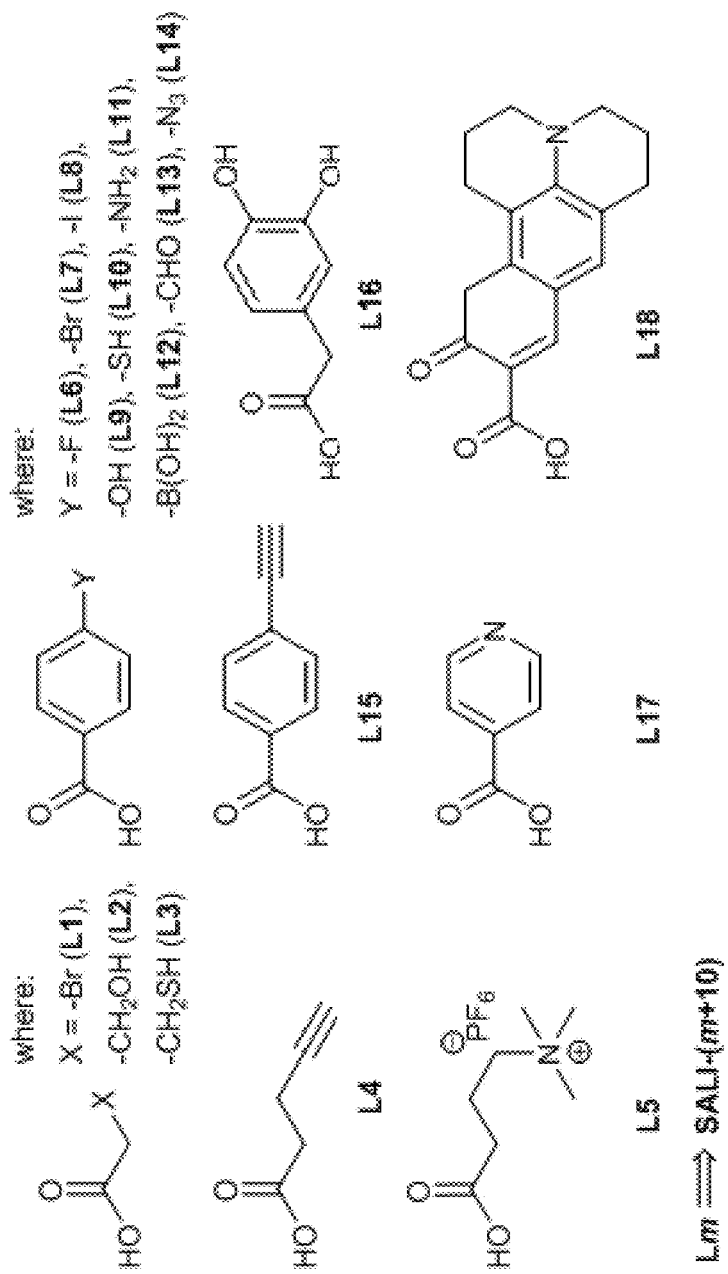
FIG. 6. Carboxylic functional groups (CFGs) incorporated through SALI into NU-1000.
Figure 7:
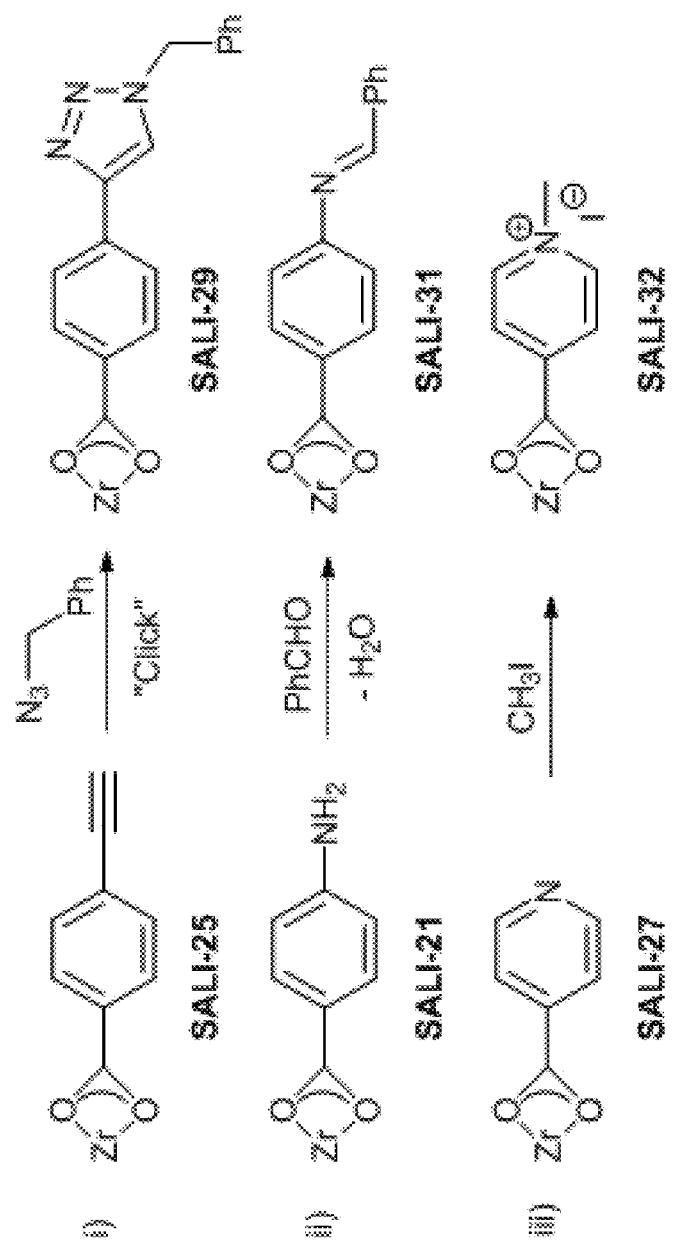
FIG. 7. Secondary functionalization reactions: i) "click", ii) imine condensation and iii) methylation, involving SALI derivatives of NU-1000.

As noted above, it has been found that the as-synthesized form of NU-1000, termed NU-1000/BA, contains residual benzoate ligands at the node sites subsequently occupied by pairs of terminal hydroxides; see FIG. 1. Benzoate is present because benzoic acid is used as a modulator in the synthesis of NU-1000. FIGS. 6 and 7 show the range of carboxylates subsequently incorporated. For the majority of these, SALI proved possible only after removal of coordinated benzoate (by extended treatment of the as-synthesized material with aq. HCl in DMF at ca. 80° C.). $^1$H NMR spectroscopic evidence confirmed benzoate removal. N$_2$ adsorption isotherms showed that the removal was accompanied by a significant increase in N$_2$-accessible pore volume.

A brief description of the materials and methods used in this example is provided here. For more detail, see the "Detailed Materials and Methods" section below. New carboxylate ligands were incorporated in activated microcrystalline samples of NU-1000 by exposing the samples to solutions of 10 equiv. of CFG per Zr$_6$-node in polar solvents such as N,N-dimethylformamide (DMF), dimethyl sulfoxide (DMSO), acetonitrile (MeCN) or their mixtures at 60° C. for 24 h. For CFGs featuring lower pK$_a$ values than that of benzoic acid (e.g., compounds L1 or L6; FIG. 6) direct reaction of the ligand with NU-1000/BA was possible, with the substitution of benzoate by the CFG conjugate base occurring quantitatively. SALI reactions required a careful choice of a chemically compatible solvent—specifically, one that provided CFG solubility and that assisted the acid-base chemistry involved with SALI reaction, including removal of the H$_2$O side product. It is worth noting that SALI was unsuccessful in solvent mixtures containing water. In most cases, DMF was successfully employed. For L1, L4 and L15 (FIG. 6), however, SALI was unsuccessful in DMF, due to the formation and subsequent reaction of dimethylamine. This problem was overcome by using as solvent a 1:3 v:v mixture of DMSO and CH$_3$CN. For quantitative SALI of L16 (FIG. 6), pure MeCN proved suitable. Following SALI, the newly functionalized samples of NU-1000 were soaked in fresh solvent to remove unreacted ligands. The samples were then thermally activated (i.e. solvent was removed) under reduced pressure.

The extent of CFG incorporation was estimated by $^1$H NMR spectroscopy after dissolving each SALI-treated compound in a 10% D$_2$SO$_4$/DMSO-d$_6$ mixture. The corresponding signals of the incorporated CFG (Scheme 1) were integrated against that of the TBAPy ligand. Depending on the identity of the CFG, between 2 and 4 CFGs were incorporated per Zr$_6$ node within NU-1000 (Table 2).

It is useful to note that complete functionalization entails the incorporation of four carboxylate ligands per node, and results in an idealized-UiO-66-like node coordination environment. (See, P. Deria, J. E. Mondloch, E. Tylianakis, P. Ghosh, W. Bury, R. Q. Snurr, J. T. Hupp and O. K. Farha, J. Am. Chem. Soc., 2013, 135, 16801-16804; "Deria et al.") The functionalized materials were termed SALI-n (i.e. SALI-11 through SALI-28 where the CFG corresponding to number is given in FIG. 7). The maximum incorporation for each CFG ligand was established by placing the functionalized SALI-n material into a fresh CFG solution for a second cycle of reaction.

Each of the functionalized materials was examined by powder X-ray diffraction (PXRD). The PXRD patterns for all SALI-n materials showed no sign of degradation of the parent framework; slight differences in relative diffraction peak intensities were observed, due to changes in electron density introduced by CFG ligands. (Deria et al.) Thermogravimetric analysis (TGA) showed that the stability of the SALI-n materials depended on the identity of the corresponding CFG ligand.

The porosity of each SALI-n material was evaluated by recording 77 K N$_2$ adsorption isotherms. In each case, there was a reduction in gas uptake and Brunauer-Emmet-Teller (BET) surface area (values ranged from 600-1700 m$^2$/g) in comparison to the parent material (Table 2). Slight shifts of the mesoporous step at approximately 0.22 P/P$_0$ to lower pressures in the adsorption isotherm were seen, evidencing lowering of the channel diameter upon CFG incorporation (Table 2).

Further evidence regarding the availability of secondary functional groups in SALI-n was provided by diffuse reflectance infrared Fourier transform spectroscopy (DRIFTS) measurements. In NU-1000, a peak appeared at 3674 cm$^{-1}$ which has been assigned to the terminal —OH groups, while a shoulder at 3671 cm$^{-1}$ was consistent with the bridging $\mu_3$-OH groups observed for UiO-66. (Deria et al.) For SALI-n, apart from the remaining bridging —OH ligands observed at 3671 cm$^{-1}$, signature peaks relevant to the secondary functional groups could be clearly discerned: for example, ethyne stretching in SALI-25 appeared at 2119 cm$^{-1}$ and similarly characteristic peaks relevant to the incoming functional groups in SALI-21, SALI-23 and SALI-24, could be discerned at 3485/3382, 1710, and 2123 cm$^{-1}$ respectively.

To demonstrate the chemical accessibility and utility of the MOF-incorporated CFGs, various secondary functionalization reactions were performed. Summarized in FIG. 7 are three representative examples: an acetylide/azide "click" reaction (SALI-25), imine formation (SALI-21), and quaternization of nitrogen base (SALI-27). These widely used, high-yield secondary functionalization reactions were aimed at: a) incorporating new functionalities that are not compatible with a free carboxylate moiety, b) facilitating introduction of various metal-Schiff base catalysts, and c) demonstrating incorporation of tethered ionic species potentially relevant to separations, catalysis and/or sensing.

A copper (I) catalyzed "click" reaction of benzyl azide with SALI-25 was carried out in the presence of sodium ascorbate in DMSO with 62% yield after 2 h as determined by $^1$H NMR spectroscopy. DRIFTS data highlighted the disappearance of the ethynyl stretching peak at 2119 $cm^{-1}$ after the "click" reaction. While the PXRD pattern for the "click" product, SALI-29, indicated retention of the framework structure, an $N_2$ isotherm revealed lower surface area and pore volume upon such secondary functionalization. Likewise, the azide moiety in SALI-24 was successfully "clicked" with phenylethyne. Similarly, SALI-21 converted to the imine derivative SALI-31 with quantitative yield (FIG. 7) as confirmed by $^1$H NMR and DRIFTS data. While a quantitative quaternization reaction of the pyridine moiety in SALI-27 was observed following methyl iodide (MeI) treatment, no methanol was detected in the $^1$H and $^{13}$C NMR spectrum, thus indicating that the $\mu_3$-OH functionality remained intact under these conditions.

In summary, it has been shown that NU-1000 can be used as a platform material in conjunction with the utility of SALI to efficiently incorporate various carboxylic acid-based alkyl and aromatic secondary functional groups. The wide range of CFGs that can be incorporated via SALI points to a battery of potential utilities in chemical separations, catalysis, and storage. Successful secondary functionalization (e.g. click reactions and imine formation) enhances the scope the already wide scope of SALI implied, and demonstrates the stability of materials synthesized by SALI for those functionalities that are not compatible with acid.

Detailed Materials and Methods for Example 2

Materials

Reagents and Solvents:
Acetone (Macron, 98%), acetonitrile (Macron, 99.8%), dimethyl sulfoxide (DMSO) (Aldrich, 99.8%, anhydrous), N,N-dimethylformamide (DMF) (Macron, 99.8%), dichloromethane (Macron, 99.0%), deuterated dimethyl sulfoxide ($d_6$-DMSO) (Cambridge Isotopes, 99%), deuterated sulfuric acid ($D_2SO_4$) (Cambridge Isotopes, 96-98% solution in $D_2O$) were used as received without further purification. Compounds L1-L15. L17 and L18 were purchased from Aldrich, while compound L16 was obtained from Combi-Blocks; these compounds were used without further purification. Benzyl azide (Alfa Aesar), benzaldehyde (GFS), $CuSO_4.5H_2O$ (Aldrich), and (1H,1H,2H,2H-tridecafluorooct-1-yl)phosphonic acid (SynQuest lab) were used as received.

Microcrystalline NU-1000 was prepared via solvothermal method according to a published procedure. (See, Mondloch et al.)

Secondary Structural Element:
Based on single crystal X-Ray diffraction data it was found that ~20-25% of the mesoporous channels of the NU-1000 contain a secondary structural element. This secondary element can be represented as $[Zr_6(\mu_3\text{-}O)_4(\mu_3\text{-}OH)_4]_2(TBAPy)_6$ which connects to 12 $Zr_6$ nodes of the parent framework through six TBAPy ligands. Residual electron density plots from X-Ray diffraction studies and gas sorption studies supported by molecular simulations were included and discussed in more detail in the reference 1. It is important to note that complete functionalization upon SALI entails incorporation four carboxylates ligands per node, and results in an idealized-UiO-66-like node coordination environment in the SALI-n materials; presence of the secondary structural element does not alter the total number of CFGs incorporated into the MOF.

NU-1000 Formulation:
The alternative molecular formulation of the $Zr_6$-based node in NU-1000 structure would feature bridging oxo and terminal aquo ligands in place of hydroxo ligands. For simplicity, only the hydroxo alternative is referred to; however both formulations should yield the observed ligand incorporation chemistry.

Instrumentation.
Powder X-ray diffraction (PXRD) patterns were recorded on a Rigaku ATXG diffractometer equipped with an 18 kW Cu rotating anode, MLO monochromator, and a high-count-rate scintillation detector (measurements made over a range of 1.5°<2θ<30° in 0.05° step width with a 2 deg/min scanning speed). $^1$H NMR spectra were recorded on Agilent 400 MHz instrument; samples were digested in 10% $D_2SO_4$/DMSO-$d_6$. Diffuse reflectance infrared spectra (DRIFTS) were recorded on a Nicolet 7600 FTIR spectrometer equipped with an MCT detector. The spectra were collected in a KBr mixture under $N_2$ purge (samples were prepared under air); KBr was utilized as the background. Nitrogen isotherms were measured on a Micromeritics TriStar II 3020 at 77 K; for BET surface area analyses the two consistency criteria described by Rouquerol et al. and Walton et al. were satisfied. Pore size distribution was calculated using Barrett-Joyner-Halenda (BJH) method with Halsey thickness curve and Kruk-Jaroniec-Sayari correction applied. Thermogravimetric analysis (TGA) was performed on a Mettler Toledo TGA under $N_2$ flow and heated from room temperature to 700° C. (at 10° C./min).

Synthesis and Characterization of SALI-n from NU-1000 ($Zr_6(\mu_3\text{-}OH)_8(OH)_8(TBAPy)_2$).

A 45 mg portion of activated NU-1000 (0.021 mmol) was loaded into a 5 mL microwave vial (Biotage). Subsequently 3 mL of a 0.07 M solution of CFG (0.21 mmol) in a polar solvent (Table 2) were added to the reaction vial, which was then sealed and heated at 60° C. for 18-24 h with occasional swirling. The supernatant of the reaction mixture was decanted and the MOF sample was soaked in fresh hot solvent, filtered, washed sequentially with acetone/acetonitrile and dichloromethane (60, 40 and 30 mL each), and finally dried under air.

TABLE 2

SALI metrics, BET surface area, pore volume, and BJH pore width of the SALI derived materials.

| CFG compound | SALI SALI-n condition | CFG/$Zr_6$-node | BET [$m^2$/g] | Pore volume [$cm^3$/g] | BJH pore width [Å] |
|---|---|---|---|---|---|
| NU-1000 | — — | — | 2315 | 1.40 | 30.5 |
| NU-1000/BA | — — | 4 | 1520 | 0.90 | 28.0 |

TABLE 2-continued

SALI metrics, BET surface area, pore volume, and BJH pore width of the SALI derived materials.

| CFG compound | SALI SALI-n | SALI condition | CFG/Zr$_6$-node | BET [m$^2$/g] | Pore volume [cm$^3$/g] | BJH pore width [Å] |
|---|---|---|---|---|---|---|
| L1 | 11 | MeCN | 4 | 1050 | 0.65 | 30.0 |
| L2 | 12 | DMF | 3.5 | 1150 | 0.72 | 30.5 |
| L3 | 13 | DMF | 3.5 | 1730 | 0.95 | 30.0 |
| L4 | 14 | 1:1 DMSO:MeCN | 2 | 1220 | 0.78 | 30.0 |
| L5 | 15 | MeCN | 2 | 1070 | 0.74 | 30.5 |
| L6 | 16 | 1:4 DMSO:MeCN | 4 | 1025 | 0.63 | 29.0 |
| L7 | 17 | DMF | 4 | 1180 | 0.67 | 27.0 |
| L8 | 18 | DMF | 4 | 1430 | 0.75 | 26.0 |
| L9 | 19 | DMF | 3.5 | 595 | 0.36 | 30.0 |
| L10 | 20 | DMF | 4 | 1115 | 0.61 | 27.5 |
| L11 | 21 | DMF | 2.5 | 1160 | 0.67 | 28.5 |
| L12 | 22 | DMF | 3 | 1245 | 0.69 | 28.5 |
| L13 | 23 | DMF | 3 | 1240 | 0.67 | 27.0 |
| L14 | 24 | DMF | 4 | 1750 | 1.05 | 30.0 |
| L15 | 25 | 1:1 DMSO:MeCN | 3 | 1580 | 0.89 | 30.0 |
| L16 | 26 | MeCN | 4 | 1010 | 0.63 | 28.5 |
| L17 | 27 | DMF | 3.8 | 1455 | 0.78 | 28.0 |
| L18 | 28 | DMF | 2 | 1415 | 0.92 | 28.5 |

Secondary Reactions with SALI-n.
"Click" Reaction with SALI-25:

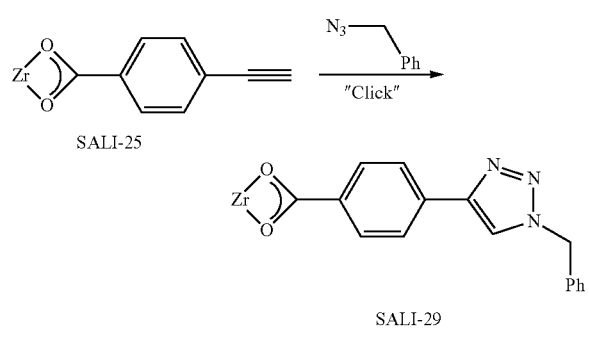

A 45 mg portion of activated SALI-25 (0.02 mmol; ~0.06 mmol of L15) was loaded into a 5 mL microwave vial (Biotage) that contained a 2 mL portion of DMSO. Sodium ascorbate (4.7 mg, 0.024 mmol), benzyl azide (15 μL, 0.12 mmol) and CuSO$_4$.5H$_2$O (2 mg, 0.012 mmol dissolved in 100 μL DMF) were subsequently added to the reaction vial, which was then sealed and heated at 60° C. for 3 h with occasional swirling. The MOF sample was then filtered, washed sequentially with DMSO, acetonitrile and dichloromethane (60, 40 and 30 mL each), and finally air dried. "Click" reaction yield: ~62%

"Click" Reaction with SALI-24:

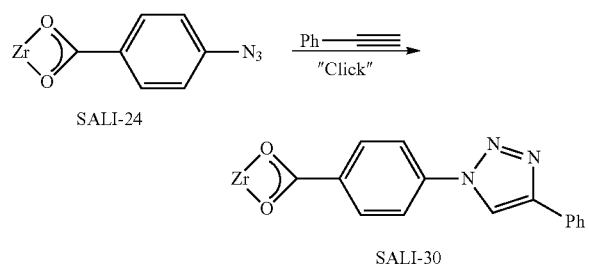

A 40 mg portion of activated SALI-24 (0.022 mmol; ~0.09 mmol of L14) was loaded in a 5 mL microwave vial (Biotage) that contained a 2 mL portion of DMSO. Sodium ascorbate (1.80 mg, 0.009 mmol), phenylacetylene (12 μL, 0.10.9 mmol) and CuSO$_4$.5H$_2$O (0.72 mg, 0.0045 mmol dissolved in 72 μL DMF) were subsequently added to the reaction vial, which was then sealed and heated at 60° C. for 3 h with occasional swirling. The MOF sample was then filtered, washed sequentially with DMSO, acetonitrile and dichloromethane (60, 40 and 30 mL each), and finally air dried. "Click" reaction yield: ~60%.

Imine Condensation Reaction with SALI-21:

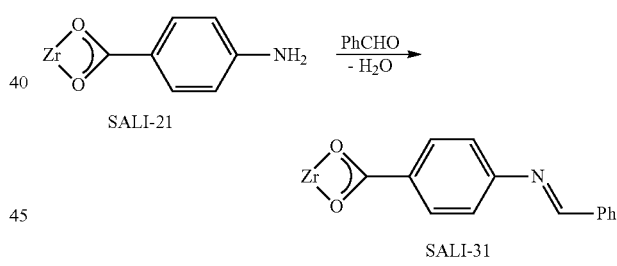

21 mg of activated SALI-21 (0.009 mmol; 0.018 mmol of L11) were loaded into a 5 mL microwave vial (Biotage) and 2 mL of ethanol were added. Benzaldehyde (36 μL, 0.36 mmol) was subsequently added to the reaction vial, which was then sealed and heated at 85° C. for 48 h with occasional swirling. The MOF sample was then filtered, washed 3 times with ethanol and dried at 120° C. under oil pump vacuum for 12 h yielding SALI-31 material.

Methylation Reaction with SALI-27:

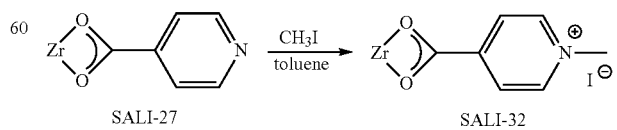

20 mg of activated SALI-27 (0.008 mmol; 0.016 mmol of 17) were loaded into a 5 mL microwave vial (Biotage) and 2 mL of toluene were added. Methyl iodide (10 μL, 0.16 mmol) was subsequently added to the reaction vial, which was then sealed and heated at 85° C. for 48 h with occasional swirling. The MOF sample was then filtered, washed with toluene and then 3 times with acetone and dried at 120° C. under oil pump vacuum for 12 h yielding SALI-32 material.

Conversion Rate of SALI-n.

Depending on the identity of the CFG, between 2 and 4 CFGs were incorporated per $Zr_6$ node within NU-1000 (Table 2). Higher ligand acidity ($pK_a$ of the COOH of the incoming ligand) and lower ligand steric demand resulted in higher degrees of MOF functionalization. The maximum incorporation for each CFG ligand was established by placing the functionalized SALI-n material, obtained after 24 h of reaction, into a fresh CFG solution for a second cycle of reaction of 24 h; in most cases the $2^{nd}$ cycle did not result in higher incorporation. Likewise the rate of incorporation can also be expected to depend on the acidity and steric of incoming ligand. To further elucidate this point pyridine-4-carboxylic acid (L17) was reacted with NU-1000 as a function of time under similar condition. The $^1$H NMR spectra of the resulting materials (SALI-27) indicated the conversion of NU-1000 to SALI-27 was complete within an hour time. Rate of conversion for the secondary reactions were also estimated to be completed in 2-3 h time.

It should be noted that the time required recovering the solid SALI-n materials from the reaction mixture, either by filtration or centrifugation is about 10-15 min which adds a significant error when studying the reaction progress at a time point that is less than 1 h.

Pore Size Distributions for NU-1000 and SALI-n.

The $N_2$ adsorption isotherms of the CFG—functionalized SALI-n samples showed similar features as compared to the parent NU-1000: all $N_2$ adsorption isotherms are type IVc. Brunauer-Emmett-Teller (BET) analyses of the isotherms (Table 2) indicate a decrease in surface area from 2315 $m^2/g$ for NU-1000 to 600-1750 $m^2\ g^{-1}$ for SALI-n samples depending on the degree of incorporation and the steric hindrance of the CFG. Likewise, the pore size distribution was calculated using Barrett-Joyner-Halenda method (BJH). The pore volumes (Table 2) were also decreased for SALI-n samples as a function of space occupied by the incorporated CFG ligands, i.e. depending on the degree of functionalization and size of the CFG. A comparison of the isotherms and corresponding BJH pore size distributions for the parent NU-1000 and two SALI derivatives, SALI-18 (NU-1000/4-idobenzoic acid) and SALI-27 (NU-1000/isonicotinic acid) showed a systematic decrease of the pores size.

TGA for NU-1000 and SALI-n.

TGA data showed that the thermal stability of SALI-n materials mainly depended on the stability of the incorporated CFG ligand. For example, in case of SALI-24 (NU-1000/4-azidobenzoic acid) decomposition of azido ligand took place, similarly for SALI-32 (NU-1000/(Melxisonicotinic acid)) weight loss at 150° C. could observed due to the removal of MeI.

Example 3

This example illustrates the phosphonate-based SALI of NU-1000 using a representative non-bridging ligand, phenylphosphonate (PPA). Additionally, it: a) compares the chemical stability (especially acid and base stability) of the SALI-PFG compound (PFG=phosphonate functional group) to that of a representative SALI-CFG compound (CFG=carboxylate functional group), SALI-BA where BA is benzoate, and b) illustrates conditions that permit sequential SALI of different ligands to be achieved.

Materials:

Acetone (Macron, 98%), N,N-dimethylformamide (DMF) (Macron, 99.8%), dichloromethane (Macron, 99.0%), deuterated dimethyl sulfoxide ($d_6$-DMSO) (Cambridge Isotopes, 99%), and deuterated sulfuric acid (Cambridge Isotopes, 96-98% solution in $D_2O$) were used as received without further purification. Phenylphosphonic acid was purchased from Aldrich. $H_4$TBAPy [1,3,6,8-tetrakis(p-benzoic-acid)pyrene] was synthesized as previously described. (See, Mondloch, et al.)

Microcrystalline NU-1000 was prepared solvothermally according to a published procedure. (See, Mondloch, et al.) For the activation of the as-synthesized material (including removal of ligated and free benzoate/benzoic acid), DMF (12 mL in total) and 0.5 mL of 8 M HCl (aq) were added to the isolated solid and the resulting suspension was heated at 100° C. oven for 18-24 h. After cooling to room temperature, the suspension was centrifuged (5 min, 7000 rpm) and washed (3×12 mL) with fresh DMF. The residual solid was soaked and washed with acetone (4×15 mL), and finally dried in a vacuum (~100 torr) oven for 30 min at 50° C. to yield ~50 mg of activated MOF.

Instrumentation:

Powder X-ray diffraction (PXRD) patterns were recorded on a Rigaku ATXG diffractometer equipped with an 18 kW Cu rotating anode, MLO monochromator, and a high-count-rate scintillation detector (measurements made over a range of $1.5°<2\theta<30°$ in 0.05° step width with a 2 deg/min scanning speed). $^1$H and $^{19}$F NMR spectra were recorded on an Agilent 400 MHz instrument after digesting the samples in 10% $D_2SO_4$/DMSO-$d_6$: the $^{19}$F signals of the trifluoroacetic acid was integrated against the $^1$H NMR signals of the TBAPy ligand using an internal standard (2,5-dibromo-1,4-bis(trifluoromethyl)benzene. Diffuse reflectance Fourier transformed infrared spectra (DRIFTS) were recorded on a Nicolet 7600 FTIR spectrometer equipped with an MCT detector. The spectra were collected in a KBr mixture. Scanning electron microscopy (SEM) images and energy dispersive X-ray spectroscopy (EDS) mapping were recorded on a Hitachi SU8030 SEM. Nitrogen isotherms were measured on a Micromeritics TriStar II 3020 at 77 K; for BET surface area analyses the consistency criteria described by Rouquerol et al. and Walton et al. were satisfied. (See, Rouquerol, J.; Llewellyn, P.; Rouquerol, F. *Stud. Surf Sci. Catal.* 2007, 160, 49 and Walton, K. S.; Snurr, R. Q. *J. Am. Chem. Soc.* 2007, 129, 8552.) Pore size distributions were calculated using the Barrett-Joyner-Halenda (BJH) method with Halsey thickness curve and Kruk-Jaroniec-Sayari correction applied.

Synthesis of SALI-BA: This material, featuring four benzoates per node, is simply the as-synthesized form of NU-1000, which was sequentially washed with DMF and acetone (4×10 mL each for 100 mg sample) prior to thermal activation at 120° C. for 12 h.

Synthesis of SALI-PPA: Exploratory syntheses were done by combining NU-1000 with 0.013-0.027 M PPA solutions. Notably, these are from 5 to 10 times less concentrated than those typically used for a SALI-CFG reaction. To obtain a version of SALI-PPA featuring ca. four phenylphosphonate ligands per $Zr_6$ node, a 45 mg portion of activated NU-1000 (0.021 mmol) was placed into a 4-dram vial (VWR). Subsequently, a 0.027 M solution of HPPA (0.102 mmol; ~4.42 equiv per $Zr_6$ node) in DMF was added to the reaction vial, which then was capped and heated at 55° C. for 18 h with occasional swirling. The reaction mixture was centrifuged (7000 rpm, 5 min) and the sedimented SALI-PPA sample was soaked in fresh solvent, centrifuged, washed sequentially with DMF (5×10 mL), acetone (5×10 mL), and dichloromethane (3×10 mL), and finally dried in a vacuum oven at 60° C. $^1$H NMR spectra, collected after dissolving the MOF samples in a 10% $D_2SO_4$/DMSO-$d_6$ mixture, confirmed that approximately four phenyl phosphonates per $Zr_6$ node were incorporated.

SALI-PPA@2 (NU-1000 decorated with, on average, ca. two phenylphosphonate ligands per $Zr_6$ node) was similarly prepared, except that a 0.013 M solution of HPPA (0.051 mmol; ~2.65 equiv per $Zr_6$ node) in DMF as solvent was used.

Stability Tests:

A 45 mg portion of SALI-BA or SALI-PPA (~0.017 mmol) was exposed to 5 mL of 0.2 M solution (corresponding to a 10-fold molar excess of reagent relative to the total BA or PPA ligand present) of various acids or bases in organic or aqueous media for 18-24 h. The pH of the aqueous solutions was varied by using acids with different $pK_a$ values: 0.2 M aqueous solutions of acetic acid (pH≈4.2), formic acid (pH≈2.0), and hydrochloric acid (pH≈0.5). Also used were aq. N-ethylmorpholine (pH≈10.5) and aq. 0.01 M NaOH. After the MOFs were treated with the respective chemical solution, the reaction mixture was centrifuged (7000 rpm, 5 min) and the sedimented MOF sample was soaked in fresh solvent, centrifuged, washed sequentially with DMF (5×10 mL), acetone (5×10 mL), and dichloromethane (3×10 mL), and finally dried in a vacuum oven at 60° C. These samples were then characterized by PXRD, collection of $N_2$ sorption isotherms and DRIFTS.

Synthesis and Characterization of SALI-PPA

Since dibasic phosphonates form strong bonds with high-valent transition metals, including $Zr^{IV}$, synthesizing SALI-PPA materials required milder conditions than used previously for incorporating carboxylates. In particular, it proved essential to limit added PPA to stoichiometric (4 per $Zr_6$) or substoichiometric amounts. When larger than stoichiometric amounts were used, appreciable release of $TBAPy^{4-}$ linker was detected. Presumably, when present in excess, PPA is substituting not only for water and hydroxo ligands but also for the linker. In fact, even under stoichiometric synthesis conditions a modest amount of linker loss occurred (ca. 8%; as detected from the absorption spectra of the supernatant recovered from the SALI reaction). In contrast, with stoichiometric or substantial excess carboxylate ligand no linker loss was observed during SALI.

Returning to PPA, $^1$H NMR measurements for digested samples showed that the extent of SALI be varied from roughly 2 PPA ligands per node to roughly 4 simply by varying the concentration of HPPA between 0.013 M and 0.27 M (i.e. ~2 and ~4 equivalents of PPA for the volume of solution and mass of MOF used). The incompletely decorated material was termed SALI-PPA@2 to distinguish it from a fully decorated form. SEM images of the latter show that phosphonate ligand incorporation does not detectably change the size or shape of the MOF crystallites.

Figure 12:
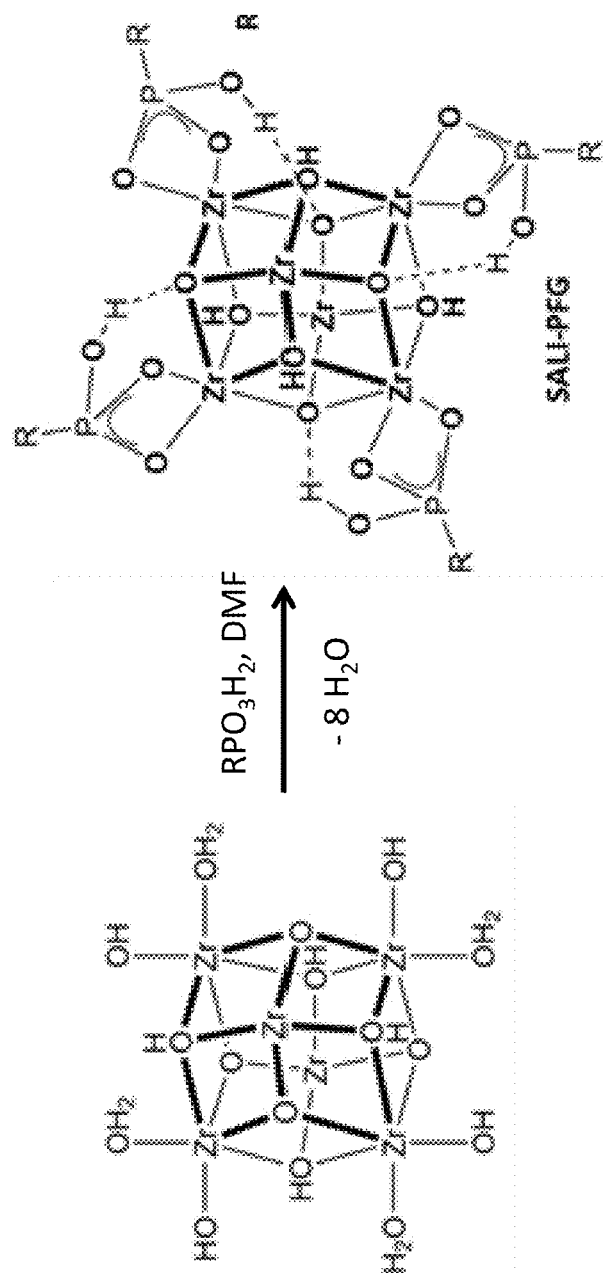
FIG. 12 shows the primary carboxylate-based SALI of NU-1000.

The work with carboxylate ligands established that SALI of four such ligands per node yields a local coordination environment that closely resembles that for a hypothetical defect-free version of UiO-66, i.e. twelve carboxylates total, with four $\mu_3$-hydroxo and four $\mu_3$-oxo ligands. Together these twenty ligands present a charge of −24 that is fully balanced by six tetravalent zirconium ions. Similar charge-balancing considerations led us to a determination that a dibasic phosphonate ligand $RPO_2(OH)^-$ binds to a node by chelating (with two oxygen atoms) a terminal Zr(IV), leaving one acidic proton (P—O—H) to hydrogen bond with either a $\mu_3$-oxo ligand of the node or with residual solvent molecules (FIG. 12).

Diffuse reflectance infrared Fourier transform spectroscopic (DRIFTS) data, showed peaks at 1145, 1133, and 1066 cm$^{-1}$ that are consistent with phosphorous-oxygen stretches for phosphonate featuring two coordinated oxygen atoms and one P—O—H with the characteristic P—OH peak appearing at 2300-2350 cm$^{-1}$. Peaks assignable as O—H stretches appeared in the 3600-3700 cm$^{-1}$ region. The intense peak at 3674 cm$^{-1}$ for underivatized NU-1000 is assigned to both terminal and bridging O—H stretches. Notably, this peak was significantly attenuated for SALI-PPA@2 and yet further attenuated for SALI-PPA. Nevertheless, some intensity remained (in contrast the peak is fully eliminated for SALI-BA.) The residual intensity indicates a detectable degree of unfunctionalized hydroxyl and aqua ligands at the node termini. Unfortunately, attempts to push the SALI process to completion by increasing the quantity of initially used HPPA resulted in MOF degradation as evidenced by release of $TBPy^{4-}$, as already noted. Indeed, even with stoichiometric (4:1) addition of HPPA to the MOF, slight degradation was observed, as evidenced again by release of ca. 8% of the $TBPy^{4-}$ initially present in the framework.

Returning to the DRIFTS spectrum for SALI-PPA, peaks for additional O—H stretches were observed at 3660 and 3650 cm$^{-1}$. While the former can be assigned to the residual bridging $\mu_3$-O—H stretch (a corresponding transition in the SALI-BA sample appeared at 3671 cm$^{-1}$), the latter is associated the acidic phosphonate O—H unit, as its intensity diminished upon treatment with an organic base. Lastly, a broad band at 3614 cm$^{-1}$ was evident. By analogy to a similarly shaped peak (at ~3653 cm$^{-1}$) for SALI-BA, the band was assigned to H-bonded moieties.

MOF porosities were evaluated via $N_2$ adsorption isotherm measurements at 77 K. All four versions of the MOF yielded type IVc isotherms. Assessments of Brunauer-Emmett-Teller (BET) surface areas (Table 3) showed that channel functionalization with either PPA or BA engendered small, but easily detectable, decreases. The total amount of gas taken up is similarly changed by SALI-based functionalization. Moreover, the $N_2$ adsorption isotherms exhibited a shift in the mesoporosity step at $P/P_0$=0.25 for unmodified NU-1000 to lower pressures for the functionalized materials. This result is consistent with loading-dependent decreases in micropore volume and channel diameter (see Table 3).

The crystallinity of the phosphonate-functionalized materials was assessed by powder X-ray diffraction (PXRD). The PXRD patterns for all SALI-PPA materials showed no sign of degradation of the crystallinity of the parent framework, although there were slight changes in relative diffraction peak intensities, due to changes in the electron density introduced by the functionalized ligands.

TABLE 3

BET Surface Areas, Pore Diameters, and Pore Volumes for NU-1000 and SALI-derived Variants

| MOF | Ligand | Ligand: $Zr_6{}^a$ | BET Surface Area (m$^2$ g$^{-1}$) | BJH Pore diameter (Å) | Pore Vol. (cm$^3$ g$^{-1}$) |
|---|---|---|---|---|---|
| NU-1000 | —OH, —H$_2$O | | 2145 | 31 | 1.46 |
| SALI-BA | PhCO$_2$— | 4.0 | 2005 | 28 | 1.21 |

TABLE 3-continued

BET Surface Areas, Pore Diameters, and Pore
Volumes for NU-1000 and SALI-derived Variants

| MOF | Ligand | Ligand: $Zr_6{}^a$ | BET Surface Area ($m^2\,g^{-1}$) | BJH Pore diameter (Å) | Pore Vol. ($cm^3\,g^{-1}$) |
|---|---|---|---|---|---|
| SALI-PPA@2 | PhPO$_2$(OH)— | 2.4 | 1920 | 30 | 1.27 |
| SALI-PPA | PhPO$_2$(OH)— | 4.1 | 1720 | 29 | 1.12 |

Chemical Stability of SALI-BA and SALI-PPA

To assess the chemical stability of the installed-ligand/MOF-node bonding in SALI-PPA and SALI-BA, and to gain further insight into the nature of the bonding in SALI-PPA, the two materials were challenged with various chemical conditions: i) hot water, ii) HCl solution in DMF, iii) aqueous acid and base solutions, and iv) organic acid and base solutions.

First, the SALI-derived samples (SALI-BA, and SALI-PPA) were soaked in water at 100° C. for 24 h. Subsequent analysis via $^1$H NMR spectroscopy indicated little, if any, ligand loss, and essentially no change in framework porosity or crystallinity.

SALI-derived samples were treated with 0.2 M aqueous acid solutions (5 mL each) with varying pH (realized by using acids with different pK$_a$s with constant reagent concentration; see discussion of Stability tests, above). Similar degrees of ligand loss (~12-25% by $^1$H NMR), but no significant linker (TBAPy$^{4-}$) leaching, were detected for SALI-BA and SALI-PPA. Subsequent N$_2$ isotherm measurements indicated 85 to 96% porosity retention for SALI-BA and 94 to 98% retention for SALI-PPA, as judged by BET surface areas. PXRD patterns were unchanged.

Treatment with aqueous base provided a more distinctive picture of the relative (ligand and framework) chemical stabilities of the BA and PPA functionalized samples. Exposure to 0.2 M aqueous N-ethylmorpholine led to loss of 70% of the BA ligand (of SALI-BA), while the SALI-PPA sample suffered a loss of only ~40% of its phosphonate ligand. After exposure to a more basic solution (pH 12.0), the SALI-BA sample lost 80% of its benzoate ligands, while SALI-PPA lost 60% of PPA ligands. The frameworks for both versions remained intact in the aqueous basic solutions as evidenced by PXRD and porosity measurements.

Finally, 45 mg samples of SALI-BA and SALI-PPA were exposed to a mixture of 8M HCl (0.5 mL) in DMF (12 mL) at 100° C. for 24 h. These conditions lead to quantitative removal of ligated benzoate. In striking contrast, zero ligand loss was detected for SALI-PPA.

The combined results clearly indicate that the phosphonate ligands are more tenaciously bound to the Zr$_6$ node than are monotopic carboxylates. Additionally, the results of base exposure indicate that PPA incorporation renders the parent material slightly more resistant to hydroxide attack and framework dissolution.

Ligand Binding Mode in SALI-PPA

Exposure to an organic base, piperidine (pK$_a$ of the conjugated acid ~11) in DMF, left SALI-BA essentially unchanged: $^1$H NMR data indicated no loss of BA ligands, no residual base, and no change in N$_2$ BET surface area. In contrast, $^1$H NMR data for a digested sample of a piperidine-exposed sample of SALI-PPA revealed incorporation of 0.8 piperidines per PPA ligand. An attractive interpretation consistent with the mode of phosphonate coordination proposed in FIG. 12, is reaction of the added base with PPA's P—O—H moiety. DRIFTS data for the piperidine-exposed SALI-PPA sample clearly showed diminished band intensities at 3662, and 3650 cm$^{-1}$ relative to the 3674 cm$^{-1}$ transition. Among these, the band at 3650 cm$^{-1}$ was especially affected by the piperidine treatment, suggesting that the transition is associated with the acidic hydroxyl group of the bound phosphonate ligand. A broad band at 3598 cm$^{-1}$ is attributed to an H-bonded species formed by the piperidinium moiety with the Zr$_6$ bound phosphonate, hydroxyl, and residual solvents; note a corresponding band in the SALI-PPA sample, prior to piperidine treatment, appeared at 3614 cm$^{-1}$. Regardless of the assignments, it is clear that piperidine binds via an acid/base interaction that is unavailable in SALI-BA. Thermogravimetric analysis (TGA) data showed ~8% mass loss at 250° C. as expected for the ~1 piperidine per PPA ligand (calculated ~10%).

Consecutive SALI

Exposure of SALI-BA and SALI-PPA samples to 0.2 M trifluoroacetic acid (HTFA) solution in DMF as solvent yielded contrasting results. While all the benzoate ligands in the SALI-BA sample were replaced by trifluoroacetate, no loss of phenylphosphonate was detected for SALI-PPA sample. Complete replacement of the benzoate ligands in SALI-BA with trifluoroacetate is consistent with the finding that the conjugate base of the carboxylic acid possessing the lower pK$_a$ is more competitive for node ligation than is the conjugate base of the carboxylic acid featuring the higher pK$_a$. In contrast, no PPA ligand loss (via replacement) was observed in the SALI-PPA sample by trifluoroacetate even though HPPA is a weaker acid (pK$_{a1}$=1.83) than HTFA (pK$_a$=0.5). These data clearly suggest that bound phosphonate ligands at the Zr$_6$ nodes manifest robust anchors compared to their carboxylate analogues and establish that it is not only the Brönsted acidity of the conjugate of the incoming anionic ligand that drives a SALI reaction but also the strength of the newly formed metal-ligand bond(s).

Interestingly, $^{19}$F NMR spectra indicated incorporation of ~1 trifluoroacetate ligand per Zr$_6$ node in the SALI-PPA sample (now denoted SALI-PPA/TFA) following exposure to a HTFA solution, without significant change in BET surface area or pore volume. Since the SALI-PPA sample contains a modest fraction of unfunctionalized, terminal-Zr (IV) sites, a reasonable explanation for TFA incorporation is an additional SALI reaction, but now with a ligand (a carboxylate) that is not strongly interacting enough to initiate partial MOF dissolution. DRIFTS data for the SALI-PPA/TFA sample were consistent with a consecutive-SALI scenario. Thus, the residual O—H intensity at 3674 cm$^{-1}$ for SALI-PPA was absent for SALI-PPA/TFA, and was replaced by a new peak at 3668 cm$^{-1}$. Elemental mapping analyses via SEM-EDS indicate that the trifluoroacetate ligand was distributed evenly over MOF crystal and thus, providing clues about the distribution of unfunctionalized sites after the PPA SALI reaction.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A ligand-coordinated metal-organic framework compound comprising a plurality of metal nodes coordinated by organic molecular linkers, wherein at least some of the metal nodes are coordinated to phosphonate ligands via phosphonate oxygen atoms or a combination of phosphonate ligands via phosphonate oxygen atoms and carboxylate ligands via carboxylate oxygen atoms.

2. The compound of claim 1, wherein the metal nodes are $Zr_6$ nodes.

3. The compound of claim 2, wherein the organic molecular linkers comprise TBAPy groups.

4. The compound of claim 2, wherein at least some of the $Zr_6$ nodes are coordinated to carboxylate ligands via carboxylate oxygen atoms.

5. The compound of claim 2, wherein at least some of the $Zr_6$ nodes are coordinated to carboxylate ligands via carboxylate oxygen atoms and at least some of the $Zr_6$ nodes are coordinated to phosphonate ligands via phosphonate oxygen atoms.

6. The compound of claim 2, wherein the carboxylate ligands or phosphonate ligands comprise an alkyl group.

7. The compound of claim 6, wherein the alkyl group is a fluorinated alkyl group.

8. The compound of claim 2, wherein the carboxylate ligands or phosphonate ligands comprise an aryl group.

9. A method of coordinating ligands to a metal-organic framework compound that comprises a plurality of metal nodes coordinated by organic molecular linkers, wherein at least some of the metal nodes are terminated by one or more hydroxyl groups, the method comprising: exposing the metal-organic framework compound to a solution comprising phosphonic acid group-containing molecules, or a combination of phosphonic acid group-containing molecules and carboxylic acid group-containing molecules, under conditions at which the terminal hydroxyl groups react with the carboxylic acid groups or the phosphonic acid groups to form phosphonate ligands coordinated to the metal nodes via phosphonate oxygen atoms or a combination of phosphonate ligands coordinated to the metal nodes via phosphonate oxygen atoms and carboxylate ligands coordinated to the metal nodes via carboxylate oxygen atoms.

10. The method of claim 9, wherein the metal nodes are $Zr_6$ nodes.

11. The method of claim 10, wherein the organic molecular linkers comprise TBAPy groups.

12. The method of claim 10, wherein at least some of the $Zr_6$ nodes are coordinated to carboxylate ligands via carboxylate oxygen atoms and at least some of the $Zr_6$ nodes are coordinated to phosphonate ligands via phosphonate oxygen atoms.

13. The method of claim 10, wherein the carboxylate ligands or phosphonate ligands comprise an alkyl group.

14. The method of claim 13, wherein the alkyl group is a fluorinated alkyl group.

15. The method of claim 10, wherein the carboxylate ligands or phosphonate ligands comprise an aryl group.

16. The method of claim 9, further comprising reacting the carboxylate or phosphonate ligands with secondary reactant molecules to form secondary carboxylate or phosphonate ligands coordinated to the metal nodes.

17. The method of claim 9, comprising exposing the metal-organic framework compound to a solution comprising phosphonic acid group-containing molecules under conditions at which some of the terminal hydroxyl groups react with the phosphonic acid groups to form phosphonate ligands coordinated to the metal nodes via phosphonate oxygen atoms and subsequently exposing the metal-organic framework compound to a solution comprising carboxylic acid group-containing molecules under conditions at which at least some of the remaining terminal hydroxyl groups react with the carboxylic acid groups to form carboxylate ligands coordinated to the metal nodes via carboxylate oxygen atoms.

18. A method of sequestering carbon dioxide using the ligand-coordinated metal-organic framework compound of claim 1, wherein the carboxylate ligands, phosphonate ligands or both are fluorinated, the method comprising: exposing the ligand-coordinated metal organic framework compounds to an environment containing carbon dioxide molecules, wherein carbon dioxide molecules are adsorbed by the ligand-coordinated metal organic framework compound and thereby removed from the environment.

19. The method of claim 18, further comprising removing the adsorbed carbon dioxide molecules from the ligand-coordinated metal organic framework compound.

20. A ligand-coordinated metal-organic framework compound comprising a plurality of metal nodes coordinated by organic molecular linkers, wherein at least some of the metal nodes are coordinated to carboxylate ligands via carboxylate oxygen atoms.

21. The compound of claim 20, wherein the metal nodes are $Zr_6$ nodes.

22. The compound of claim 21, wherein the organic molecular linkers comprise TBAPy groups.

23. The compound of claim 21, wherein the carboxylate ligands comprise an alkyl group.

24. The compound of claim 23, wherein the alkyl group is a fluorinated alkyl group.

25. The compound of claim 21, wherein the carboxylate ligands comprise an aryl group.

26. A method of coordinating ligands to a metal-organic framework compound that comprises a plurality of metal nodes coordinated by organic molecular linkers, wherein at least some of the metal nodes are terminated by one or more hydroxyl groups, the method comprising: exposing the metal-organic framework compound to a solution comprising carboxylic acid group-containing molecules under conditions at which the terminal hydroxyl groups react with the carboxylic acid groups to form carboxylate ligands coordinated to the metal nodes via carboxylate oxygen atoms.

27. The method of claim 26, wherein the metal nodes are $Zr_6$ nodes.

28. The method of claim 27, wherein the organic molecular linkers comprise TBAPy groups.

29. The method of claim 27, wherein the carboxylate ligands comprise an alkyl group.

30. The method of claim 29, wherein the alkyl group is a fluorinated alkyl group.

31. The method of claim 27, wherein the carboxylate ligands comprise an aryl group.

32. The method of claim 26, further comprising reacting the carboxylate ligands with secondary reactant molecules to form secondary carboxylate ligands coordinated to the metal nodes.

33. A method of sequestering carbon dioxide using the ligand-coordinated metal-organic framework compound of claim 20, wherein the carboxylate ligands are fluorinated, the method comprising: exposing the ligand-coordinated metal organic framework compounds to an environment containing carbon dioxide molecules, wherein carbon dioxide molecules are adsorbed by the ligand-coordinated metal organic framework compound and thereby removed from the environment.

34. The method of claim 33, further comprising removing the adsorbed carbon dioxide molecules from the ligand-coordinated metal organic framework compound.

* * * * *